(12) United States Patent
De Scheerder et al.

(10) Patent No.: US 8,267,991 B2
(45) Date of Patent: Sep. 18, 2012

(54) INTRALUMINAR PERFORATED RADIALLY EXPANDABLE DRUG DELIVERY PROSTHESIS AND A METHOD FOR THE PRODUCTION THEREOF

(75) Inventors: Ivan De Scheerder, Herent (BE); Jurgen Sohier, Leuven (BE); Natasja van der Leden, Zeist (NL); Jan Van Humbeeck, Hassrode (BE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 12/714,954

(22) Filed: Mar. 1, 2010

(65) Prior Publication Data

US 2010/0152836 A1 Jun. 17, 2010

Related U.S. Application Data

(63) Continuation of application No. 11/353,601, filed on Feb. 14, 2006, now Pat. No. 7,789,907, which is a continuation of application No. 09/798,990, filed on Mar. 6, 2001, now Pat. No. 7,135,039.

(30) Foreign Application Priority Data

Mar. 6, 2000 (EP) ..................................... 00870035

(51) Int. Cl.
*A61F 2/06* (2006.01)
(52) U.S. Cl. ..................................... 623/1.42
(58) Field of Classification Search ................ 623/1.15, 623/1.16, 1.38–1.46, 1.13
See application file for complete search history.

(56) References Cited

U.S. PATENT DOCUMENTS

| | | | |
|---|---|---|---|
| 4,580,568 A | 4/1986 | Gianturco | |
| 5,242,399 A | 9/1993 | Lau | |
| 5,314,444 A | 5/1994 | Gianturco | |
| 5,421,955 A | 6/1995 | Lau | |
| 5,443,477 A | 8/1995 | Marin | |
| 5,449,373 A * | 9/1995 | Pinchasik et al. | ............. 606/198 |
| 5,494,029 A | 2/1996 | Lane | |
| 5,496,277 A | 3/1996 | Termin | |
| 5,507,771 A | 4/1996 | Gianturco | |
| 5,514,154 A | 5/1996 | Lau et al. | |

(Continued)

FOREIGN PATENT DOCUMENTS

DE 19916086 10/1999

(Continued)

OTHER PUBLICATIONS

Antithrombotic Therapy after Coronary Stenting; American Heart Journal; 138(4): 663-669. 1999; Mosby—Year Book, Inc.; U.S.A.

(Continued)

*Primary Examiner* — Alvin J. Stewart
(74) *Attorney, Agent, or Firm* — Vidas, Arrett & Steinkraus, P.A.

(57) ABSTRACT

A radially expandable prosthesis for implantation in a lumen comprises a tubular wall having an inner surface and an outer surface. The tubular wall is provided with cuts to form solid struts which have a thickness and which enables the prosthesis to expand. The solid struts have reservoirs made therethrough in the form of perforating holes for containing a therapeutic agent. The perforating holes each have an inner opening and an outer opening of substantially the same size. The prosthesis, including said perforating holes, has a smooth electrochemically polished surface.

17 Claims, 9 Drawing Sheets

U.S. PATENT DOCUMENTS

| | | | |
|---|---|---|---|
| 5,531,741 A | 7/1996 | Barbacci | |
| 5,591,197 A * | 1/1997 | Orth et al. | 623/1.16 |
| 5,603,721 A | 2/1997 | Lau | |
| 5,718,713 A * | 2/1998 | Frantzen | 623/1.15 |
| 5,725,572 A * | 3/1998 | Lam et al. | 623/1.16 |
| 5,735,893 A * | 4/1998 | Lau et al. | 623/1.16 |
| 5,741,293 A | 4/1998 | Wijay | |
| 5,755,776 A * | 5/1998 | Al-Saadon | 623/1.15 |
| 5,776,161 A * | 7/1998 | Globerman | 606/194 |
| 5,797,898 A | 8/1998 | Santini et al. | |
| 5,807,404 A * | 9/1998 | Richter | 623/1.16 |
| 5,824,037 A | 10/1998 | Fogarty et al. | |
| 5,824,040 A | 10/1998 | Cox et al. | |
| 5,827,321 A * | 10/1998 | Roubin et al. | 623/1.16 |
| 5,843,164 A * | 12/1998 | Frantzen et al. | 623/1.16 |
| 5,868,781 A * | 2/1999 | Killion | 623/1.15 |
| 5,868,782 A * | 2/1999 | Frantzen | 623/1.15 |
| 5,902,266 A | 5/1999 | Leone | |
| 5,913,895 A | 6/1999 | Burpee | |
| 5,916,264 A * | 6/1999 | Von Oepen et al. | 623/1.15 |
| 5,922,021 A * | 7/1999 | Jang | 623/1.15 |
| 5,925,061 A | 7/1999 | Ogi et al. | |
| 5,931,866 A * | 8/1999 | Frantzen | 623/1.15 |
| 5,954,743 A * | 9/1999 | Jang | 623/1.15 |
| 5,972,027 A | 10/1999 | Johnson | |
| 6,017,365 A * | 1/2000 | Von Oepen | 623/1.15 |
| 6,022,371 A * | 2/2000 | Killion | 606/198 |
| 6,033,433 A * | 3/2000 | Ehr et al. | 623/1.16 |
| 6,036,725 A * | 3/2000 | Avellanet | 623/1.13 |
| 6,039,756 A * | 3/2000 | Jang | 623/1.15 |
| 6,042,597 A * | 3/2000 | Kveen et al. | 623/1.15 |
| 6,056,776 A * | 5/2000 | Lau et al. | 623/1.16 |
| 6,066,169 A * | 5/2000 | McGuinness | 623/1.16 |
| 6,068,656 A * | 5/2000 | Von Oepen | 623/1.17 |
| 6,071,305 A | 6/2000 | Brown et al. | |
| 6,123,721 A * | 9/2000 | Jang | 623/1.15 |
| 6,129,755 A * | 10/2000 | Mathis et al. | 623/1.15 |
| 6,132,461 A * | 10/2000 | Thompson | 623/1.15 |
| 6,156,062 A | 12/2000 | McGuinness | |
| 6,179,868 B1 | 1/2001 | Burpee | |
| 6,183,506 B1 * | 2/2001 | Penn et al. | 623/1.15 |
| 6,190,406 B1 * | 2/2001 | Duerig et al. | 623/1.2 |
| 6,235,053 B1 * | 5/2001 | Jang | 623/1.15 |
| 6,241,762 B1 | 6/2001 | Shanley | |
| 6,254,632 B1 | 7/2001 | Wu et al. | |
| 6,261,319 B1 * | 7/2001 | Kveen et al. | 623/1.15 |
| 6,273,908 B1 | 8/2001 | Ndondo-Lay | |
| 6,287,628 B1 | 9/2001 | Hossainy et al. | |
| 6,325,821 B1 * | 12/2001 | Gaschino et al. | 623/1.15 |
| 6,325,824 B2 * | 12/2001 | Limon | 623/1.2 |
| 6,331,188 B1 | 12/2001 | Lau | |
| 6,334,870 B1 * | 1/2002 | Ehr et al. | 623/1.16 |
| 6,342,067 B1 * | 1/2002 | Mathis et al. | 623/1.15 |
| 6,348,065 B1 * | 2/2002 | Brown et al. | 623/1.16 |
| 6,355,058 B1 * | 3/2002 | Pacetti et al. | 623/1.15 |
| 6,375,676 B1 * | 4/2002 | Cox | 623/1.16 |
| 6,375,677 B1 * | 4/2002 | Penn et al. | 623/1.16 |
| 6,379,379 B1 * | 4/2002 | Wang | 623/1.15 |
| 6,379,381 B1 | 4/2002 | Hossainy et al. | |
| 6,395,326 B1 | 5/2002 | Castro et al. | |
| 6,409,754 B1 * | 6/2002 | Smith et al. | 623/1.16 |
| 6,416,539 B1 * | 7/2002 | Hassdenteufel | 623/1.15 |
| 6,416,543 B1 * | 7/2002 | Hilaire et al. | 623/1.16 |
| 6,419,692 B1 * | 7/2002 | Yang et al. | 623/1.15 |
| 6,443,982 B1 * | 9/2002 | Israel et al. | 623/1.17 |
| 6,451,049 B2 * | 9/2002 | Vallana et al. | 623/1.15 |
| 6,461,380 B1 * | 10/2002 | Cox | 623/1.17 |
| 6,461,381 B2 * | 10/2002 | Israel et al. | 623/1.15 |
| 6,471,721 B1 * | 10/2002 | Dang | 623/1.34 |
| 6,475,235 B1 * | 11/2002 | Jayaraman | 623/1.15 |
| 6,506,437 B1 | 1/2003 | Harish et al. | |
| 6,508,834 B1 * | 1/2003 | Pinchasik et al. | 623/1.16 |
| 6,511,505 B2 * | 1/2003 | Cox et al. | 623/1.16 |
| 6,551,353 B1 | 4/2003 | Baker et al. | |
| 6,551,838 B2 | 4/2003 | Santini et al. | |
| 6,558,415 B2 * | 5/2003 | Thompson | 623/1.16 |
| 6,558,422 B1 | 5/2003 | Baker | |
| 6,558,733 B1 | 5/2003 | Hossainy et al. | |
| 6,562,065 B1 | 5/2003 | Shanley | |
| 6,562,067 B2 * | 5/2003 | Mathis | 623/1.16 |
| 6,596,021 B1 * | 7/2003 | Lootz | 623/1.16 |
| 6,602,281 B1 * | 8/2003 | Klein | 623/1.15 |
| 6,613,079 B1 * | 9/2003 | Wolinsky et al. | 623/1.15 |
| 6,616,689 B1 * | 9/2003 | Ainsworth et al. | 623/1.16 |
| 6,616,690 B2 * | 9/2003 | Rolando et al. | 623/1.16 |
| 6,626,935 B1 * | 9/2003 | Ainsworth et al. | 623/1.15 |
| 6,638,300 B1 * | 10/2003 | Frantzen | 623/1.15 |
| 6,652,579 B1 * | 11/2003 | Cox et al. | 623/1.34 |
| 6,656,162 B2 | 12/2003 | Santini et al. | |
| 6,663,662 B2 | 12/2003 | Pacetti et al. | |
| 6,663,664 B1 | 12/2003 | Pacetti | |
| 6,676,697 B1 * | 1/2004 | Richter | 623/1.16 |
| 6,709,379 B1 | 3/2004 | Brandau et al. | |
| 6,730,116 B1 * | 5/2004 | Wolinsky et al. | 623/1.16 |
| 6,743,252 B1 * | 6/2004 | Bates et al. | 623/1.15 |
| 6,746,479 B1 * | 6/2004 | Ehr et al. | 623/1.16 |
| 6,758,860 B1 * | 7/2004 | Penn et al. | 623/1.16 |
| 6,764,507 B2 * | 7/2004 | Shanley et al. | 623/1.16 |
| 6,770,088 B1 * | 8/2004 | Jang | 623/1.16 |
| 6,783,543 B2 | 8/2004 | Jang | |
| 6,805,705 B2 * | 10/2004 | Hong et al. | 623/1.15 |
| 6,805,707 B1 * | 10/2004 | Hong et al. | 623/1.16 |
| 6,805,709 B1 | 10/2004 | Schaldach et al. | |
| 6,818,014 B2 * | 11/2004 | Brown et al. | 623/1.16 |
| 6,846,323 B2 * | 1/2005 | Yip et al. | 623/1.16 |
| 6,849,089 B2 | 2/2005 | Stoll | |
| 6,875,227 B2 * | 4/2005 | Yoon | 623/1.16 |
| 6,896,697 B1 * | 5/2005 | Yip et al. | 623/1.15 |
| 6,896,698 B2 * | 5/2005 | Rolando et al. | 623/1.16 |
| 6,916,336 B2 * | 7/2005 | Patel et al. | 623/1.16 |
| 7,029,492 B1 * | 4/2006 | Mitsudou et al. | 623/1.15 |
| 7,044,965 B1 | 5/2006 | Spielberg | |
| 7,056,338 B2 | 6/2006 | Shanley | |
| 7,060,090 B2 * | 6/2006 | Thornton | 623/1.15 |
| 7,060,093 B2 * | 6/2006 | Dang et al. | 623/1.42 |
| 7,083,642 B2 | 8/2006 | Sirhan et al. | |
| 7,128,756 B2 * | 10/2006 | Lowe et al. | 623/1.15 |
| 7,131,993 B2 * | 11/2006 | Gregorich | 623/1.16 |
| 7,135,039 B2 * | 11/2006 | De Scheerder et al. | 623/1.42 |
| 7,160,321 B2 * | 1/2007 | Shanley | 623/1.42 |
| 7,163,555 B2 | 1/2007 | Dinh | |
| 7,169,178 B1 | 1/2007 | Santos et al. | |
| 7,169,179 B2 | 1/2007 | Shanley et al. | |
| 7,195,648 B2 * | 3/2007 | Jones et al. | 623/1.16 |
| 7,264,633 B2 * | 9/2007 | Bonsignore | 623/1.15 |
| 7,344,563 B2 | 3/2008 | Vallana et al. | |
| 7,479,158 B2 * | 1/2009 | Gregorich | 623/1.16 |
| 7,686,843 B2 * | 3/2010 | Moore | 623/1.16 |
| 2001/0047199 A1 * | 11/2001 | Wijay | 623/1.15 |
| 2002/0038145 A1 | 3/2002 | Jang | |
| 2002/0038146 A1 | 3/2002 | Harry | |
| 2003/0125803 A1 | 7/2003 | Vallana et al. | |
| 2004/0024449 A1 | 2/2004 | Boyle | |
| 2004/0034337 A1 | 2/2004 | Boulais et al. | |
| 2004/0204750 A1 | 10/2004 | Dinh | |
| 2006/0129231 A1 | 6/2006 | De Scheerder | |
| 2006/0149354 A1 | 7/2006 | Shanley et al. | |
| 2006/0195176 A1 | 8/2006 | Bates et al. | |
| 2006/0212109 A1 | 9/2006 | Sirhan et al. | |
| 2006/0224234 A1 | 10/2006 | Jayaraman | |

FOREIGN PATENT DOCUMENTS

| | | |
|---|---|---|
| EP | 0747069 | 12/1996 |
| EP | 0931520 | 7/1999 |
| EP | 0950386 | 10/1999 |
| WO | 96-09020 | 3/1996 |
| WO | 97-33534 | 9/1997 |
| WO | 9823228 | 6/1998 |
| WO | 98-30173 | 7/1998 |
| WO | 9851238 | 11/1998 |
| WO | 9916386 | 4/1999 |
| WO | 99-49928 | 10/1999 |
| WO | 9956907 | 11/1999 |
| WO | 01-66036 | 9/2001 |

OTHER PUBLICATIONS

Ivan De Scheerder, Eric Verbeken, and Jan Van Humbeeck; Metallic surface modification, Semin Intervent Cardiol 1998;3: 139-144; W.B. Saunders Company, Ltd.

R.A. White, M.D. and M.R. Back; Peripheral Endovascular Interventions, 1999 Second Edition; pp. 228-230; Springer-Verlag; New York; U.S.A.

C. Beythien, M.A. Brockmann, T. Meinertz, P Kuhnl and K Gutensohn; Biocompatibility to Reduce Thrombogenicity of Intracoronary Stents; Infusionstherapie Transfusionsmed 1999; 26 (suppl 2): 37-41.

Michael JB Kutryk and Patrick W. Serruys, Complications of Coronary Stenting, Coronary Stenting: Current Perspectives, A Companion to the Handbook of Coronary Stents, pp. 226, 256; 1999 Martin Dunitz Ltd, London.

A.F. Watkinson, E.P. Strecker and I. Boos, Metallic Stents: individual designs and characteristics, Textbook of Metallic Stents; Andreas Adam, Robert F. Dondelinger, Peter R. Mueller, eds.; 1997; pp. 207-231; Isis Medical Media, Oxford, UK.

Donald A. Eckard, MD, Graham Lee, MD, and Fung Y. Tsai, MD, The implications of Stents and Cyanoacrylates for the Treatment of Cerebrovascular Disease, Endovascular Neurological Intervention; Robert J. Maciunas, ed.; Library of Congress Catalog, Chapter 10, 1995; pp. 159-177; The American Association of Neurological Surgeons, Park Ridge, Illinois.

Rafael Beyar and Martin B. Leon, Functional design characteristics, Frontiers in Interventional Cardiology; Rafael Beyar et al. eds; 1997; p. 76; Martin Dunitz Ldt, London.

U.S. Appl. No. 09/357,669, filed Jul. 29, 1999, Title: Expandable Stent, Inventor: Ulf Harry Standford.

U.S. Appl. No. 60/094,540, filed Jul. 29, 1998, Title: Expandable Stent, Inventor: Ulf Harry Standford.

"Waterjet-guided lasers cut precisely" www.industrial-lasers.com/archive/1999/11/1199FEA6.html, Nov. 1, 1999, XP002176036.

Letter from Gevers & Vander Haeghen dated Aug. 14, 2003 for Application No. 01925368.1-2305.

"News-Apr. 1997" www.industrial-lasers.com/archive/1997/04/0497news.html, Apr. 1, 1997, XP002176037.

PCT Notification of Transmittal of the International Search Report or Declaration for PCT/EP01/02410, dated Sep. 14, 2001.

PCT Written Opinion for PCT/EP01/02410, dated Feb. 22, 2002.

EP Office Action mailed Mar. 9, 2012 for EP Application No. 01925368.1-2320/1261297, filed on Mar. 2, 2011.

EP Opposition proceedings dated Aug. 2, 2006-Mar. 9, 2012 for Application No. 01925368.1.

Communication from Vereenigde for Opposition proceeding regarding EP Patent No. 1 261 297, dated Apr. 10, 2012.

Provision of a Copy of the minutes in accordance with Rule 124(4) EPC for Patent No. 1 261 297, dated Jun. 11, 2012.

Communication from EPO regarding the oral proceedings of May 10, 2012, dated May 11, 2012.

Revocation of the EP Patent (Art. 101(2) EPC) and Opposition Division Decision, date Jun. 11, 2012.

* cited by examiner

INTRALUMINAR PERFORATED RADIALLY EXPANDABLE DRUG DELIVERY PROSTHESIS AND A METHOD FOR THE PRODUCTION THEREOF

CROSS-REFERENCE TO RELATED APPLICATIONS

This application is a Continuation application from U.S. patent application Ser. No. 11/353,601, filed Feb. 14, 2006, which is a Continuation application from U.S. patent application Ser. No. 09/798,990, now U.S. Pat. No. 7,135,039, filed Mar. 6, 2001, and which claims priority to European Patent Application 00870035, filed Mar. 6, 2000, the entire contents of each being incorporated herein by reference.

STATEMENT REGARDING FEDERALLY SPONSORED RESEARCH

Not Applicable

BACKGROUND OF THE INVENTION

Field of the Invention

The present invention relates to radially expandable prostheses for implantation in a lumen comprising a tubular wall produced from sheet metal and showing cuts enabling the prosthesis to expand and to a method for producing such prostheses wherein said cuts are at least partially made by means of a laser beam.

In practice, intraluminal prostheses are generally known. They can be implanted in a lumen, for example an artery, to strengthen, support or repair the lumen. With coronary balloon dilatation for example, often a prosthesis is implanted in the place where a coronary artery is injured or where it tends to collapse. Once implanted, the prosthesis strengthens that part of the artery in a way the blood flow is ensured. A prosthesis configuration which is extremely suited for implantation in a body lumen, is a generally cylindrical prosthesis which can radially expand from a first small diameter to a second larger one. Such prostheses can be implanted in the artery by placing them on a catheter and transporting them through the artery to the desired location. The catheter is provided with a balloon or another expansion mechanism which exerts a radial outwards pressure on the prosthesis so that the prosthesis expands to a larger diameter. These prostheses are sufficiently strong to stay in shape after expansion, even after removal of the catheter.

Radially expandable prostheses are available in a variety of configurations, in this way an optimal efficacy is ensured in different particular situations. The patents of Lau (U.S. Pat. Nos. 5,514,154, 5,421,955, and 5,242,399), Baracci (U.S. Pat. No. 5,531,741), Gaterud (U.S. Pat. No. 85,522,882), Gianturco (U.S. Pat. Nos. 5,507,771 and 5,314,444), Termin (U.S. Pat. No. 5,496,277), Lane (U.S. Pat. No. 5,494,029), Maeda (U.S. Pat. No. 5,507,767), Marin (U.S. Pat. No. 5,443,477), Khosravi (U.S. Pat. No. 5,441,515), Jessen (U.S. Pat. No. 5,425,739), Hickle (U.S. Pat. No. 5,139,480), Schatz (U.S. Pat. No. 5,195,984), Fordenbacher (U.S. Pat. No. 5,549,662) and Wiktor (U.S. Pat. No. 5,133,732) all contain a sort of radially expandable prosthesis for implantation in a body lumen.

The mentioned intraluminal prostheses have some disadvantages. Many of these expandable prostheses are not extremely flexible and have a central axis that remains rather linear when the prosthesis is not expanded yet. Due to such a lack of flexibility the insertion of the prosthesis in the artery to be correctly placed in the body lumen is hampered. Another problem of the intraluminal prostheses is their decrease in axial length at radial expansion. Although the patent of Lau (U.S. Pat. No. 5,514,154) attempts to reduce the axial shortening, it fails to succeed entirely.

When a prosthesis is placed in the artery or in another lumen, the implantation has to be performed precisely in the desired place. Intraluminal prostheses are often exactly placed before their expansion, but due to the expansion the axial shortening causes that the prosthesis finally does not turn up in the correct place.

In addition the determination of the exact location of a prosthesis during an implantation in a lumen is difficult, although a highly qualitative medical monitoring system is available. The problem of the exact place determination of the prosthesis enlarges the problem of the precise and exact placement. There exists a need for a radially expandable prosthesis presenting little or none axial shortening at radial expansion and that can be located without difficulty using medical imaging systems during the implantation. Another frequently occurring problem is the occlusion of the side branches. In the case of coronary arteries this can cause a myocardial infarction.

Another important problem is the insufficient hemocompatibility of intraluminal prostheses, when they are implanted intravascularly. They can cause acute or subacute thrombotic occlusions due to thrombus formation resulting in a considerable morbidity and even mortality. Furthermore these prostheses evoke a foreign body reaction with a considerable inflammation all around the prosthesis inducing fibromuscular cellular proliferation and narrowing of the prosthesis. The general object of the present invention is therefore to provide new methods and new prostheses which enable to reduce the foreign body reaction against the implanted prostheses.

Concerning the method of producing such prostheses, EP-A-0 931 520 teaches to start from a thin-walled tubular member, in particular a stainless steel tubing, and to cut this tubing to remove portions of the tubing in the desired pattern for the prosthesis or stent. This cutting process is performed by means of a computer-controlled laser. In order to minimize the heat input by the laser into the prosthesis so as to prevent thermal distortion and other damages to the metal, use is made of a Q-switched Nd/YAG laser which is operated to produce very short pulses (<100 nsec) at a high pulse rate of up to 40 kHz. Further, a gas jet is created co-axially to the laser beam. Notwithstanding the use of a gas jet, a considerable amount of debris, slag or molten material is formed along the edges of the cut which must be removed mechanically or chemically after the cutting operation. This is achieved in EP-A-0 931 520 by soaking the cut stainless tube first for eight minutes in a solution of hydrochloric acid (HCl) and by subsequently electropolishing it in an acidic aqueous solution of sulfuric acid, carboxylic acids, phosphates, corrosion inhibitors and a biodegradable surface active agent with a current density of about 0.06 to 0.23 amps per $cm^2$. A drawback of such severe chemical and electrochemical polishing processes is that the inner and outer surfaces of the tubular prosthesis may also become attacked.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

A first object of the present invention is therefore to provide a new method for cutting the prosthesis by means of a laser which enables to achieve cleaner or finer cut edges after the cutting operation and to limit the required polishing operations to achieve an optimal biocompatibility.

For this purpose, the method according to a first aspect of the invention is characterized in that for making at least a number of said cuts, said laser beam is guided in a jet of liquid towards the sheet metal.

According to the invention, it has been found that by using such a technique, which is known as water-guided laser technology, it is possible to achieve immediately cleaner cut edges and to reduce the thermal and structural distortion, in particular the deformation of the metal grain structure. In this way, the body foreign reaction against the implanted prosthesis causing narrowing to the prosthesis can thus be more easily avoided or reduced.

A second object of the present invention is to provide specific methods for electropolishing prostheses made from tantalum or from a nickel titanium alloy which also enable to improve the biocompatibility of the prosthesis.

To this end, the method according to a second aspect of the invention is characterized in that when the prosthesis is made from a nickel titanium alloy, in particular from nitinol, it is polished electrochemically in an electrolyte solution containing perchloric acid and at least one carboxylic acid, in particular acetic acid and, when the prosthesis is made from tantalum, it is polished electrochemically in an electrolyte solution containing sulfuric acid, hydrofluoric acid and optionally a carboxylic acid, in particular acetic acid.

In this second aspect of the invention, the prosthesis is also cut by means of a laser beam, preferably by means of the liquid guided laser beam according to the first aspect of the invention. By using liquid, in particular water-guided laser technology and the specific electrochemical polishing techniques this prosthesis can be rendered of a superior biocompatibility, which results in a reduced probability of thrombogenicity, neointimal hyperplasia and intraluminal narrowing of the prosthesis after intraluminal implantation.

Further improvement of the biocompatibility of the prosthesis can be obtained according to the invention by applying a titanium nitride layer having a thickness of between 0.1 and 500 µm, and preferably a thickness of between 1 and 10 µm.

In a third aspect, the invention relates to a special configuration which enables the prosthesis to release an effective amount of therapeutic agent or medicine over a prolonged period of time, in particular a medicine suppressing the foreign body reaction against the prosthesis increasing thereby also the biocompatibility of the prosthesis. The tubular wall of the prosthesis is provided with cuts forming struts having a predetermined thickness and enabling the prosthesis to expand, the struts having a longitudinal direction and showing reservoirs made in said outer surface for containing the therapeutic agent.

Such a prosthesis is already disclosed in EP-A-0 950 386. In this known prosthesis, the reservoirs are formed by relatively shallow channels which are laser cut in the outer surface of the prosthesis. A drawback of this known prosthesis is that at the location of the channels the local drug delivery will be much greater than at other locations resulting in a quite non-homogeneous distribution of the therapeutic agent. Another drawback is that the depth of the channels is limited in view of the fact that the presence of the channels have a considerable effect on the radial strength and durability of the prosthesis. Due to the limited depth, the effect of this depth on the period of drug release is consequently also limited.

In a third aspect an object of the present invention is therefore to provide a new prosthesis which enables to provide a more uniform drug release, to extend this release over a greater period of time and to incorporate the therapeutic agent in the prosthesis with a smaller effect on the radial strength thereof.

For this purpose, the prosthesis is characterized in this third aspect of the invention in that at least a number of said reservoirs are formed by holes which show at least an outer opening at the outer surface of the tubular wall and which extend over a depth in said struts larger than 30%, preferably larger than 50% and most preferably larger than 60%, of the thickness thereof, said outer opening having a width measured perpendicular to said longitudinal direction and a length measured in said longitudinal direction which comprises at the most five times, preferably at the most three times, said width.

Since the length of the holes comprises at the most five times the width thereof, more holes can be provided in the outer surface of the prosthesis, i.e. at shorter mutual distances, so that a more homogenous drug delivery is possible. A further advantage of such shorter holes is that they can be made deeper without affecting the required radial strength of the prosthesis. In this way, it is possible to incorporate more therapeutic agent in the prosthesis and to increase the release period thereof due to the fact that a larger amount of therapeutic agent can be contained in one hole relative to the surface area of the outer opening thereof through which the therapeutic agent is released. The small holes, which may show a bottom or extend entirely through the strut wherein they are made, allow to load the prosthesis with a dose of medicine up to a thousand times higher compared to a none perforated prosthesis. In this way a more biocompatible intraluminal prosthesis can be obtained which can also be used as a vehiculum for releasing and or depositing medicines locally.

In a preferred embodiment, at least a bottom portion of said hole is substantially conical, the hole having either a bottom or extending through the strut forming in said inner surface of the tubular wall an inner opening.

An important advantage of this embodiment is that the holes can be made easily by laser cutting, in particular in accordance with the liquid guided laser cutting technique, by simply directing the laser beam to the desired spot and cutting the hole without any further movement of the laser beam. The depth of the hole can then simply be controlled by adjusting the total amount of energy of the laser beam, i.e. the pulse width, the duration and the intensity thereof. When making perforating holes, the diameter of the inner opening of the holes on the inner side of the strut can be controlled in the same way, i.e. also by adjusting the amount of energy used to make the hole by means of the laser beam. In other words, the amount of therapeutic agent released towards the inside of the prosthesis can be easily controlled by selecting the desired diameter of the inner openings. The total amount of cutting energy can be increased until the inner opening is substantially as large as the outer opening.

These and other embodiments which characterize the invention are pointed out with particularity in the claims annexed hereto and forming a part hereof. However, for further understanding of the invention, its advantages and objectives obtained by its use, reference should be made to the drawings which form a further part hereof and the accompanying descriptive matter, in which there is illustrated and described a embodiments of the invention.

BRIEF DESCRIPTION OF THE SEVERAL VIEWS OF THE DRAWING(S)

Other particularities and advantages of the invention will become apparent from the following description of some particular embodiments of the method and the prosthesis according to the present invention. The reference numerals used in this description relate to the annexed drawings wherein.

DETAILED DESCRIPTION OF THE INVENTION

Figure 1:
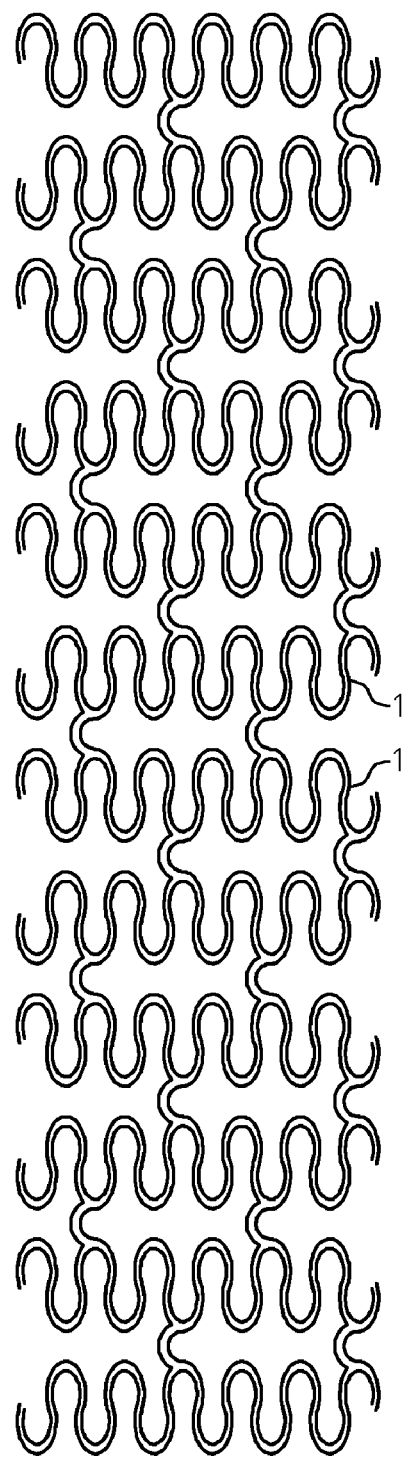
FIG. 1 is a top plan view on a tubular prosthesis which has been cut in its longitudinal direction and pressed into a flat sheet.

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

1) Description of the Basic Design of the Endovascular Prosthesis

Figure 2:
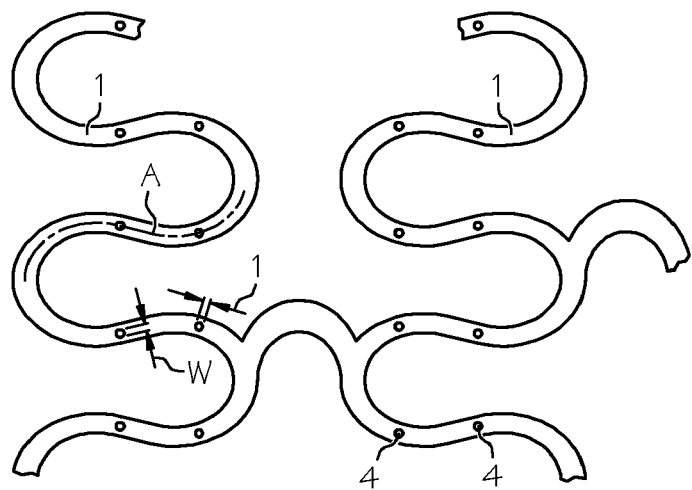
FIG. 2 shows on a larger scale a portion of the sheet illustrated in FIG. 1 and showing additionally the holes provided in the outer surface of the prosthesis.

In general the present invention relates to radially expandable prostheses for implantation in a lumen which comprise a tubular wall produced from sheet metal and showing cuts enabling the prosthesis to expand. In the method according to the invention, these cuts are at least partially made by means of a laser beam. The prosthesis is thus made starting from a tubular member wherein cuts are made, or wherein usually portions are cut away, according to the design of the prosthesis. Instead of starting from a tubular member, use could also be made of a flat sheet which is enrolled and welded together to form the tubular prosthesis. FIGS. 1 and 2 illustrate a preferred embodiment of a radially expandable prosthesis that presents little or none axial shortening at radial expansion. The prosthesis consists of filaments or struts 1 describing the outline of a cylindrical contour. Each prosthesis filament connects to a separate surface at right angles to a central axis of the cylindrical contour of the prosthesis and parallel with other surfaces of the adjacent filaments. The prosthesis can exist of a variable amount of filaments which all constitute the prosthesis. At least two filaments are necessary, including a first and a second ending filament to determine the extremities of the prosthesis contour.

These filaments all show a waving contour in the shape of consecutive omegas. Consequently each filament is composed of a number of turns with lowest points and tops zigzag crossing over the length of each filament. The lowest point is the most distant from the adjacent filament and the top is the most closely situated to the adjacent filament. FIG. 1 shows a typical configuration with 12 turns, a number that can vary from 3 to 36 turns. The size of each filament, provided as the distance between lowest point and top, changes when the prosthesis expands radially, mostly the size diminishes. In FIG. 1 a typical configuration is shown with a distance of 1.5 mm between the lowest point and top, this distance however can vary from 0.5 to 5 mm.

The end filaments are attached to adjacent intermediate filaments by means of connecting parts in the shape of an omega that act as axial elements joining two adjacent filaments. Such connecting parts are also able to fasten together intermediate filaments. Each connecting part is attached to the adjacent filaments with a first connection point to the one end of the connecting piece and a second one to the other end. Both connecting points are situated in the tops of the filaments. Thus the connecting points are bridging the distance/opening between adjacent filaments with the interstice as maximal width. Not necessarily all perforations are bridged with axial connecting parts. Separate outlined intermediate elements can be joined together by means of junctions that are connected with the intermediate elements on locations distant of the lowest points. Depending on the flexibility needs of the prosthesis a variable number of tops can be provided with connecting parts that link adjacent filaments. In case a higher flexibility is necessary, more tops will stay empty with only one connecting piece between two adjacent filaments. The prosthesis is constructed as such that during gradual expansion of the prosthesis the filament waves will in a first phase become somewhat larger and than gradually become shorter. To compensate for this shortening the omega shaped interconnections will gradually enlarge resulting in a less axial shortening during gradual expansion.

2) Water Guided Laser Technology to Cut a Metallic Intraluminal Prosthesis

Laser cutting of metallic tubes for example 316L stainless steel, nitinol, tantalum tubes or any other metallic tube causes a considerable heat release at the cutting surface, that radiates through the material. The disadvantage is that the metal structure (grain structure) is deformed and that the cutting surface becomes irregular and oxidized. This leads to a considerable foreign body reaction against the implanted prosthesis causing narrowing of the prosthesis.

Utilizing water guided laser technology (Laser-Microjet™ or comparable systems described for example in U.S. Pat. No. 5,902,499) wherein the laser beam is guided in a jet of liquid, in particular of water, to cut the omega-prosthesis we were able to diminish these disadvantages.

1) The water jet continuously removes the burnt metal particles, resulting in a better cutting surface. The water or other liquid is generally ejected out of a nozzle at a pressure of between 20 and 500 bars, more particularly at a pressure of between 100 and 300 bars and preferably at a pressure of about 150 bars. For creating the water jet, a nozzle showing an opening having an inner diameter of 20 to 100 µm, in particular an inner diameter of 40 to 60 µm, and more particularly an inner diameter of about 60 µm can be used resulting in a water jet of a similar diameter wherein the laser beam is contained due to the difference in refractive indices of the liquid and air.

2) Thanks to the continuous liquid or water-cooling, the heat penetration is lower, causing quasi no deformation of the metal grain structure.

As an example we provide here the specific conditions to apply the water guided laser cutting system. Stainless steel tubes with a diameter of 0.0625 inch (1.585 mm) with a wall thickness of 0.004 inch (0.1 mm) were placed on a continuous rotating holder and cut with a Haas laser at a frequency of 100 Hz, pulse duration of 0.15 ms, voltage 510 Volt, head or water nozzle diameter of 60 µm and water pressure of 150 bar. Comparing the samples with conventional laser cut stents, the surface looked much brighter and less blackened. SEM examination showed a much more regular surface. Implantation of these stents after degreasing, ultrasonic cleaning and sterilization in porcine coronary arteries resulted in considerably less thrombus formation adjacent to the stent filaments and a moderate inflammatory response at 6 days follow-up. At 6 weeks follow-up area stenosis was 60%. These results however compare favorably with conventional laser cut stents. Conventional laser cut stents implanted under the same conditions resulted in a total thrombotic occlusion of the stented vessel in 40% of the cases, an abundant inflammatory response at 6 days follow-up and an area stenosis of 86% at 6 weeks follow-up. This water guided laser technology can be used to cut any other coronary stent or endovascular prosthesis out of a metallic tube.

3) Electrochemical Polishing of a Metallic Intraluminal Prosthesis

Surface characteristics of metal intraluminal prosthesis are determining the human foreign body response to the intraluminal prosthesis. Therefore optimal surface characteristics are critical for the acute and late patency of an intraluminal prosthesis. To further optimize the cutting surface, specific electrochemical polishing techniques were used to optimize the surface characteristics of intraluminal prostheses. Depending on the material used, specific chemical solutions were developed for optimal electrochemical polishing of prostheses.

Basic Principles of Electropolishing

Electropolishing is a process by which metal is removed from a work piece by passage of electric current when the work piece is immersed in a liquid media (electrolyte). The work piece is connected to the anodic terminal, while the cathodic terminal is connected to a suitable conductor. Both anodic and cathodic terminals are submerged in the solution, forming a complete electrical circuit. The current applied is direct (DC) current. In this process, the work piece is dissolved, adding metal ions to the solution. When a current passes through the electrolyte, a liquid layer of anodic dissolution products is formed on the surface of the anode; this layer has a higher viscosity and greater electrical resistivity than the bulk of the electrolyte. The thickness of the liquid layer on a rough surface differs from site to site. The current density is non-uniform as result of such non-uniform liquid layer; i.e. it is higher on peaks than in crevices. Thus, peaks dissolve more rapidly than crevices, this, therefore, produces a surface-leveling effect.

Furthermore electrochemical polishing results in a superficial oxide layer (passivation) which plays also an important role in the biocompatibilisation of a foreign body.

The quantity of metal removed from the work piece is mainly proportional to the amount of current applied and the time during which the current is applied. In addition, the geometry of the work piece can affect the distribution of the current and, consequently, has an important bearing upon the amount of the metal removed in local area.

Factors Affecting the Electropolishing Process

The mode of anodic dissolution of a metal may depend on its nature, the surface state, the composition of the electrolyte, and the temperature, current density and stirring during the electropolishing process.

Electrolytes used in electropolishing should satisfy the following requirements:

1) high-quality polishing at low voltages and current densities, 2) wide working range of anodic current densities and temperature, 3) a high stability (during operation and upon storage) and long service life, 4) absence of attack on the metal when current does not flow, 5) electrolyte should consist of cheap, readily available materials and should not present any safety hazards, 6) recovery after a certain period of service should be simple, e.g. by additions of necessary components, 7) the throwing power of the bath should be good, i.e. samples of complex shape should dissolve uniformly over their entire surface, 8) the ohmic resistivity should be low, i.e. the required current density should be obtained at a low voltage, 9) the electrolyte should be suitable for use in the electropolishing of many metals.

The anodic potential, the anodic current density, and the applied voltage are the main electrical parameters of the electropolishing process. The process is controlled on the basis of the anodic current density and sometimes on the basis of the applied voltage. For any metal and electrolyte system, there should be a certain optimal anodic current density, which provides the highest-quality electropolishing.

The temperature of the electrolyte has a marked effect on the polishing quality. A range of optimum temperatures should exist for any metal-electrolyte system. A drop in the temperature increases the viscosity of the electrolyte and thus reduces the rate of diffusion of anodic dissolution products from the anode surface to the bulk of the electrolyte.

The electropolishing time should decrease with increasing current density or with decreasing initial roughness of the surface. The initial roughness and the state of the surface also affect electropolishing quality. Before electropolishing, the surfaces are preferably degreased and cleaned in organic solvents or by chemical etching in suitable solutions. Stirring is used in cases that the anode is coated with some soluble films or it is necessary to remove bubbles adhering to the surface. Stirring of the electrolyte requires an increase in the current density. The cathodes used in electropolishing should not be attacked in the polishing solution. The surface area of the cathode is preferably much greater than the surface area of the polished work piece. This ensues a more uniform current distribution, reduces cathodic polarization and reduces power losses. After the electropolishing, the work pieces should be washed with water or other solvents in order to remove residues of the electrolyte or the anodic dissolution products.

Figure 3:
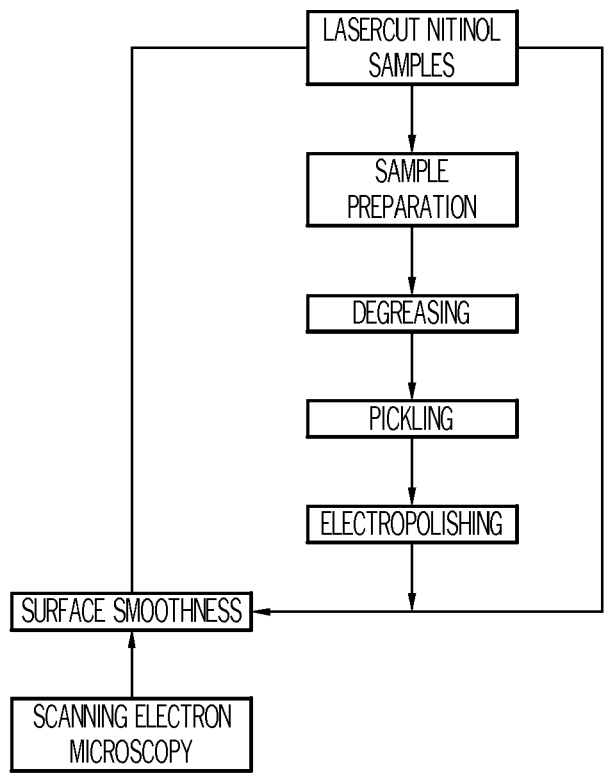
FIG. 3 is a diagram setting forth the different steps followed for the electrochemical polishing of nitinol samples.

Description of Electrochemical Polishing Techniques for Nitinol and Tantalum Endoluminal Prosthesis The electropolishing device that we used was self-designed. A glass container (150 ml) was used as container for the electrolyte. A DC rectifier (Polipower, Struers, Denmark) was employed as a power supply. A nitinol sheet material (length 15 cm, width 2.5 cm and thickness 0.2 cm) was selected as anode. As shown in FIG. 3, the as-received samples were first cleaned with an alkaline solvent with a detergent additive in an ultrasonic bath for more than ten minutes. They were then cleaned in distilled water with an ultrasonic agitation device for more than ten minutes. Since the sheet materials were covered by a black oxide film, they were pickled at room temperature in an acid solution as follows: 2 ml hydrofluoric acid (38-40%) and 40 ml nitric acid (14 M) for different time durations in a glass container (50 ml). By observation of the change of the surface state of these sheet samples, a time of seven minutes was finally chosen because the black film just disappeared at this time duration. After pickling, the samples were rinsed in distilled water with an ultrasonic agitation device for more than 10 minutes. After the preparation processes above, electropolishing was then studied with several selected electrolyte mixtures shown in Table 1. Solutions (i) and (ii) were used for electropolishing. Chemical polishing was also evaluated using the solutions (iii) and (iv) in order to have a comparison of the chemical polishing effect with electrochemical polishing.

TABLE 1

Selected mixtures for polishing nitinol alloy sheet materials

| Solution (% concentration) | Volumes |
|---|---|
| i) perchloric acid (70%) | 6 ml |
| acetic acid (99.8%) | 94 ml |
| (ii) perchloric acid (70%) | 5 ml |
| acetic acid (99.8%) | 100 ml |
| (iii) $H_2O_2$ | 50 ml |
| HF (48-51%) | 5 ml |
| (iv) $H_2O_2$ | 75 ml |
| HF (48-51%) | 5 ml |

Several conditions were selected for the different polishing mixtures in order to compare the differences in the effect of polishing and then to optimize the condition and effect of polishing, which is shown in Table 2. Firstly, as shown in Table 2 (a), the electrolyte (i) was used with a fixed applied voltage for different times to test the electropolishing conditions. The effects were evaluated visually and with optical microscopy. Secondly, the conditions of fixed time and applied voltage were studied as well as that of some other selected times (Table 2 (b)). Then, the electrolyte (ii) was used and the conditions were changed similar to those of electrolyte (i) (Table 2 (c) and Table 2 (d)). The samples were also immersed in different mixtures of acids for different times, as shown in Table 2 (e).

TABLE 2

The processing conditions for polishing nitinol alloy sheet material

Table 2 (a):

| Electrolyte | Applied Voltage (V) | Anodic current (amp) | Time (min.) |
|---|---|---|---|
| Electrolyte (i) | 30 | 0.2~0.3 | 2 |
| | | | 3 |
| | | | 4~5 |
| | | | 6 |
| | | | 8 |

Table 2 (b):

| Electrolyte | Applied Voltage (V) | Anodic current (amp) | Time (min.) |
|---|---|---|---|
| Electrolyte (i) | 5 | 0.023 | 10 |
| | 10 | 0.045 | 10 |
| | 15 | 0.1 | 10 and 15 |
| | 20 | 0.16 | 3, 15 and 10 |
| | 25 | 0.22 | 3, 5 and 10 |

Table 2 (c):

| Electrolyte | Applied Voltage (V) | Anodic current (amp) | Time (min.) |
|---|---|---|---|
| Electrolyte (ii) | 30 | 0.15~0.25 | 2 |
| | | | 3 |
| | | | 4~5 |
| | | | 6 |
| | | | 8 |
| | | | 10 |

Table 2 (d):

| Electrolyte | Applied Voltage (V) | Anodic current (amp) | Time (min.) |
|---|---|---|---|
| Electrolyte (ii) | 20 | 0.15 | 3 |
| | | | 6 |
| | 25 | 0.17 | 3 |
| | | | 6 |

Table 2 (e):

| Electrolyte | Time (min.) |
|---|---|
| Electrolyte (iii) | 3, 9, and 15 |
| Electrolyte (iv) | 3, 9, and 15 |

Most of the polishing processes were conducted at room temperature without stirring. A part of the polishing processes however was done at an elevated temperature. Also the effect of stirring on the polishing process was explored. The reason that the applied voltage was selected as one of the controlling parameters was that the current was not stationary during the process of electropolishing and the stents had a special shape of mesh so that the current density was very difficult to calculate accurately. All of the polished samples were rinsed in distilled water with an ultrasonic agitation device for more than 10 minutes and then stored in ethanol. Evaluation of the effects of the polishing was performed by means of optical microscopy and scanning electron microscopy.

Electropolishing of a Nitinol Endovascular Prosthesis, for Example a Coronary Stent The same electropolishing cell as that for the sheet material was employed. First of all, due to the finite stent samples and their high cost, electropolishing of some nitinol alloy wires of different diameters of 1 mm, 0.3 mm and 0.5 mm were performed with different parameters in order to find an optimal way of electropolishing the nitinol alloy stents. All the wires were covered with a black oxide layer. They were ground with rough abrasive paper to remove the oxide layer. The different conditions for the electropolishing are shown in Table 3.

TABLE 3

The selected processing conditions for electropolishing nitinol alloy wires

| Electrolyte | Applied Voltage (V) | Anodic current (amp) | Time (min.) |
|---|---|---|---|
| Electrolyte (ii) | 30 | 0.21 | 2, 3, 4~5, 8 |
| | 25 | 0.2 | 2, 3, 4~5, 8 |
| | 20 | 0.18 | 2, 3, 4~5, 8 |

The selection of these conditions was based on our observations of the electropolishing of sheet materials. The removal was measured with a micrometer (Mitutoyo Digimatic micrometer).

Figure 4:
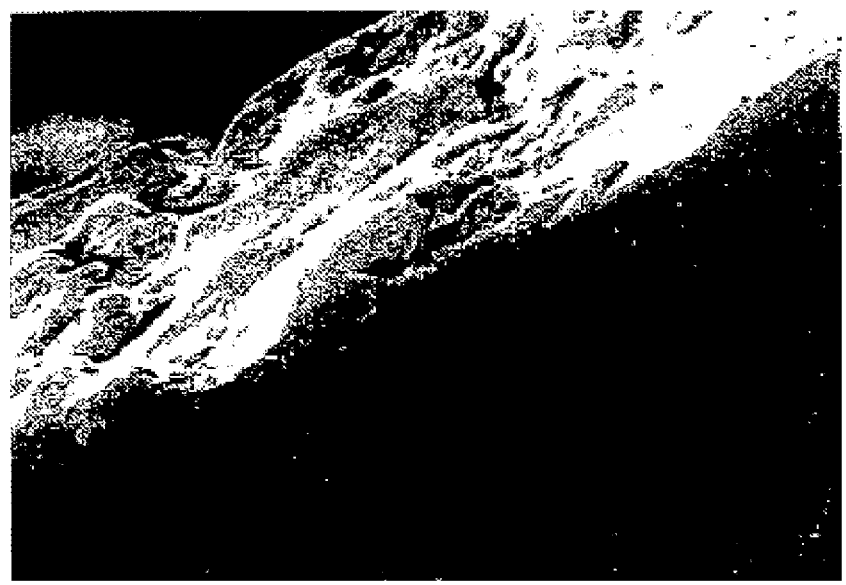
FIG. 4 is a microscopic picture (680×) showing the roughness of the side surface of a laser cut of the as-received nitinol alloy stent made by means of a conventional laser.

The as-received stents, made by means of a conventional laser cutting process and illustrated in FIG. 4, were first cleaned with an alkaline solvent with detergent additive in an ultrasonic bath for more than ten minutes in order to remove the contaminants of the surface. All the samples were then cleaned in distilled water with an ultrasonic agitation device for more than ten minutes. Considering the oxide layer formed during the process of fabrication, the stents were pickled for 2, 4 and 6 minutes at room temperature in the following acid solution: 2 ml hydrofluoric acid (38-40%) and 40 ml nitric acid (14 M).

By observation with optical microscopy, a time of nearly six minutes was chosen as the optimum pickling time of the stents. The samples were then rinsed in distilled water with ultrasonic agitation for more than 10 minutes. After pickling and rinsing, electropolishing was done without stirring at room temperature using the conditions shown in Table 4.

TABLE 4

The selected processing conditions for electropolishing nitinol alloy stents

| Electrolyte | Applied Voltage (V) | Anodic current (amp) | Time (min.) |
|---|---|---|---|
| Electrolyte (ii) | 30 | 0.25 | 3 |
| | 25 | 0.17 | 1, 1.5, 3 |
| | 20 | 0.15 | 1, 1.5~2 |

Figure 5:
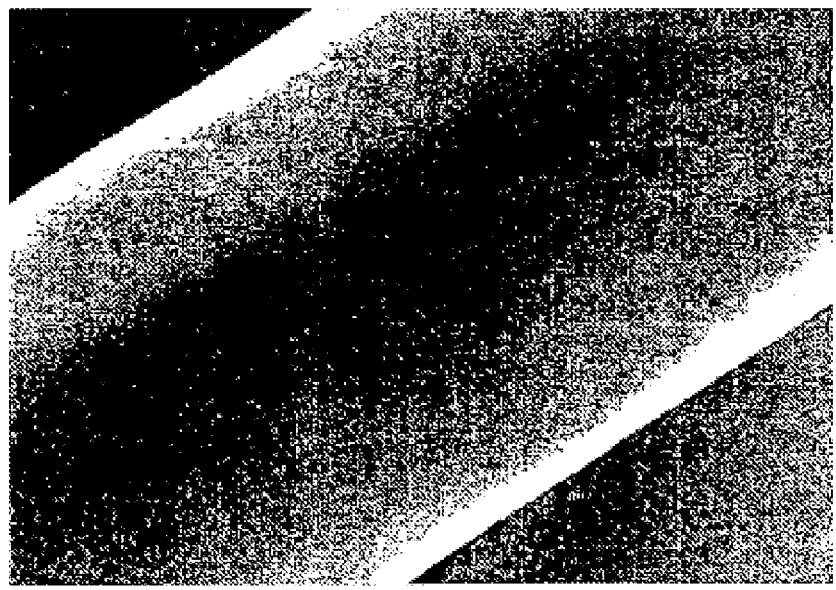
FIG. 5 is a microscopic picture (655×) of the nitinol alloy stent illustrated in FIG. 4 after having been subjected to the electrochemical polishing process.

These conditions were selected according to the results of the electropolishing of sheet materials and wires, considering the specific thin shape of mesh of the stents. After electropolishing, the samples were rinsed in distilled water with an ultrasonic agitation device for more than 10 minutes. A scanning electron microscopic picture of a electropolished stent is given in FIG. 5 illustrating the much smoother surface compared to the stent prior to electropolishing. Electropolishing of the stents without the pre-treatment of pickling was also done in order to check whether or not the oxide layer can be removed as well as to investigate the effects of pickling on the electrochemical polishing of the stents for the following condition (Table 5).

TABLE 5

The conditions for electropolishing the stents without pickling

| Electrolyte | Applied Voltage (V) | Anodic current (amp) | Time (min.) |
|---|---|---|---|
| Electrolyte (ii) | 20 | 0.15 | 1.5~2 |

Table 6 summarizes all the results of applied polishing processes process for nitinol alloy materials.

TABLE 6

The comparison of the different polishing process

Table 6 (a):

| Process | Material | Electrolyte | Applied Voltage (V) | Anodic current (amp) | Time (min.) | Result |
|---|---|---|---|---|---|---|
| Electropolishing | Sheet | Electrolyte (i)* | 30 | 0.2~0.3 | 2 | less-polished |
| | | | | | 3 | general |
| | | | | | 4~5 | good |
| | | | | | 6 | overpolished |
| | | | | | 8 | overpolished |
| | | | 5 | ~0.023 | 10 | no changes |
| | | | 10 | ~0.045 | | no changes |
| | | | 15 | ~0.1 | | small changes |
| | | | 20 | ~0.16 | | general |
| | | | 25 | ~0.22 | | general |
| | | | 15 | ~0.1 | 15 | attacked |
| | | | 20 | ~0.16 | 3 | general |
| | | | 25 | ~0.22 | | general |
| | | | 20 | ~0.16 | 5 | good |
| | | | 25 | ~0.22 | | good |

Table 6 (b):

| Process | Material | Electrolyte | Applied Voltage (V) | Anodic current (amp) | Time (min.) | Result |
|---|---|---|---|---|---|---|
| Electropolishing | Sheet | Electrolyte (ii)** | 30 | ~0.2 | 2 | general |
| | | | | | 3 | good |

TABLE 6-continued

The comparison of the different polishing process

|  |  |  |  |  | 4~5 | better |
|---|---|---|---|---|---|---|
|  |  |  |  |  | 6 | general |
|  |  |  |  |  | 8 | overpolished |
|  |  |  | 20 | ~0.15 | 3 | general |
|  |  |  | 25 | ~0.17 |  | general |
|  |  |  | 20 | ~0.15 | 6 | good |
|  |  |  | 25 | ~0.17 |  | good |
| Chemical polishing | Sheet | Electrolyte (iii)# | — | — | 3 | no changes |
|  |  |  | — | — | 9 | rough |
|  |  |  | — | — | 15 | rough |
|  |  | Electrolyte (iv)## | — | — | 3 | no changes |
|  |  |  | — | — | 9 | rough |
|  |  |  | — | — | 15 | rough |

Table 6 (c):

| Process | Material | Electrolyte | Applied Voltage (V) | Anodic current (amp) | Time (min.) | Result |
|---|---|---|---|---|---|---|
| Electropolishing | Wire | Electrolyte (ii) | 30 | ~0.21 | 2 | general |
|  |  |  |  |  | 3 | good |
|  |  |  |  |  | 4~5 | overpolished |
|  |  |  |  |  | 8 | overpolished |
|  |  |  | 25 | ~0.2 | 2 | general |
|  |  |  |  |  | 3 | good |
|  |  |  |  |  | 4~5 | overpolished |
|  |  |  |  |  | 8 | overpolished |
|  |  |  | 20 | ~0.18 | 2 | general |
|  |  |  |  |  | 3 | good |
|  |  |  |  |  | 4~5 | overpolished |
|  |  |  |  |  | 8 | overpolished |

Table 6 (d):

| Process | Material | Electrolyte | Applied Voltage (V) | Anodic current (amp) | Time (min.) | Result |
|---|---|---|---|---|---|---|
| Electropolishing | Stent | Electrolyte (ii) | 30 | ~0.25 | 3 | overpolished |
|  |  |  | 25 | ~0.17 | 1 | general |
|  |  |  |  |  | 1.5 | general |
|  |  |  |  |  | 3 | overpolished |
|  |  |  | 20 | ~0.15 | 1 | good |
|  |  |  |  |  | 1.5~2 | better |

*perchloric acid (70%) 6 ml, acetic acid (99.8%) 94 ml
**perchloric acid (70%) 5 ml; acetic acid (99.8%) 100 ml
$H_2O_2$ 50 ml, HF 5 ml
$H_2O_2$ 75 ml, HF 5 ml All these studies were conducted at room temperature without agitation. Several elevated temperatures (25° C. and 30° C.) were used, but no large changes on the results of polishing were found. As to the agitation, it gave relatively bad results for polishing sheet materials. During observation of the polishing process, dark spots appeared on the surface, and by means of optical microscopy, these surfaces were proven to be rough. In addition, bubbles were found adhering to the surface of the sample when polishing.

Two electrolytes were selected:
(i) perchloric acid (70%) 6 ml, acetic acid (99.8%) 94 ml
(ii) perchloric acid (70%) 5 ml, acetic acid (99.8%) 100 ml Finally electrolyte (ii) was selected for electrochemical polishing of either sheet materials or stents (Table 1). During experiments with electrolyte (i), no change on the surface of the sheet material was found using voltages of 5 V and 10 V, even for more than ten minutes. This is consistent with the fact that electrochemical polishing takes place only when the current density is higher than that noted at the critical point. Current density and voltage are closely related in polishing. As voltage increases there is an increase in current density generally. The surface is attacked with a voltage of 15 V for 15 minutes. This might be the effect of electroetching. Electroetching is a comparatively slow process and its current densities are often smaller than those with electropolishing. Thus, it is suggested to select the voltages of 20 V, 25 V and 30 V for this nitinol alloy material from the results in Table 6.

Figure 6:
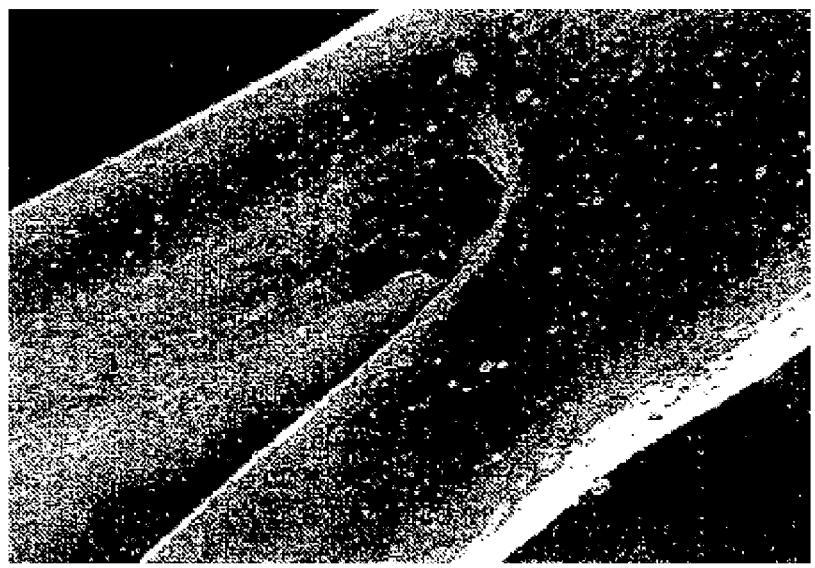
FIGS. 6 and 7 are microscopic pictures (326×) of the over polished surface of a nitinol alloy stent.
Figure 7:

The duration of polishing for sheet materials is longer than that of wires and much longer compared to that of stents. This might be because of the difference in degree of surface roughness of these materials and related to the thin size of the stent filaments. A time, up to six or eight minutes is so long that it causes over polishing for the sheet materials. However, polishing time of three minutes has caused over polishing for the stents. FIGS. 6 and 7 show two overpolished surfaces of stents. One is apparently attacked, which shows a very bad quality and the size of the stent did not remain uniform. Another one has a relatively smooth and uniform surface but the amount removed might be so large that the stent has been apparently too thin to have enough strength to be used. Thus, the amount removed from stents should be controlled very carefully so that the mechanical strength of the stent is maintained while the smoothness is obtained by means of electrochemical polishing.

The smooth surface can not be obtained by means of chemical polishing alone in this experiment. Chemical polishing is not sufficient to polish these nitinol alloy materials. The optimal conditions for electrochemical polishing of nitinol stents are shown in Table 7. These optimal conditions will be somewhat different for each particular nitinol sample and will have to be restudied for each particular nitinol prosthesis depending on the design and mesh thickness used.

TABLE 7

The optimal condition for electropolishing of nitinol alloy stents

| Electrolyte | Applied Voltage (V) | Anodic current (amp) | Time (min.) |
|---|---|---|---|
| Electrolyte (ii)** | 20 | 0.15 | 1.5~2 |

**perchloric acid (70%) 5 ml, acetic acid (99.8%) 100 ml

Based on the performed tests, the electrolyte solution used for electrochemically polishing nickel titanium alloys, in particular nitinol, comprises at least perchloric acid and at least one carboxylic acid, in particular acetic acid. In a preferred embodiment, the electrolyte solution comprises the perchloric acid and the acetic acid in a concentration corresponding to the perchloric acid and acetic acid concentrations in a mixture of 1 to 10 volume parts of a 70% by weight perchloric acid solution and 2 to 500 volume parts of a 99.8% by weight acetic acid solution, and more particularly in a concentration corresponding to the perchloric acid and acetic acid concentrations in a mixture of about 5 to about 6 volume parts, preferably about 5 volume parts, of a 70% by weight perchloric acid solution and about 94 to about 100 volume parts, preferably about 100 volume parts, of a 99.8% by weight acetic acid solution. As explained hereabove, the most preferred electrolyte solution comprises 5 volume parts of a 70% perchloric acid solution and 100 volume parts of a 99.8% acetic acid solution.

Influence of the Preparation with Acidic Pickling on Electrochemical Polishing

The conditions and results of electrochemical polishing stents with no preparation are summarized in Table 8.

TABLE 8

The result of electropolishing stents with no pickling

| Process | Material | Electrolyte | Applied Voltage (V) | Anodic current (amp) | Time (min.) | Result |
|---|---|---|---|---|---|---|
| Electropolishing | stent | Electrolyte (ii) | 20 | ~0.15 | 1.5~2 | Bad |

Figure 8:
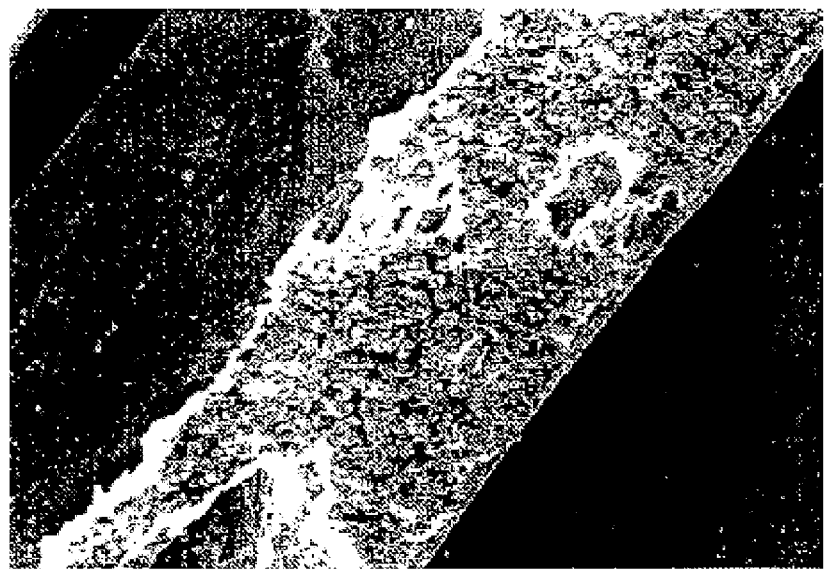
FIG. 8 is a microscopic picture (300×) of the bottom surface of an electrochemically polished nitinol alloy stent without pickling.

FIG. 8 shows the morphology of the stent surface electropolished without acidic pickling. It is very clear that the rough oxide layers still adhere to the bottom surface of the stent and reveal an even worse quality than the as-received one. Thus, it can be concluded that in case the stent is covered by a heavy oxide layer such a layer can not be removed by means of electrochemical polishing alone, i.e. the preparation of pickling is necessary for electrochemical polishing of nitinol alloy stents which are covered with heavy oxide layers.

In this experiment, acidic pickling was explored for stents at room temperature with acidic solution: 2 ml hydrofluoric acid (38-40%) and 40 ml nitric acid (14 M).

Several periods of time were selected. The description of the effects of this pickling process is summarized in Table 9.

TABLE 9

The effects of acidic pickling for preparation of electropolishing stents

| | Time (min.) | | | | |
|---|---|---|---|---|---|
| | 1 | 2 | 4 | 6 | 8 |
| Result | no change | no change | general | good | overpickled |

During the immersion times 1 min and 2 min., there was no apparent change on the surfaces compared with that of the as-received samples when studied by optical microscopy. For 4 min., 6 min. and 8 min. the oxide layers were removed. There were still some oxides adhered to the surface immersed for 4 min., whereas the oxide layer was removed completely for incubation times of 6 min. and 8 min. Thus, a time of 5 to 7 min. was selected as optimal pickling time for nitinol stents.

Polishing of a Tantalum Intraluminal Prosthesis, for Example a Coronary Stent

This study was done by means of electrochemical polishing and chemical polishing in order to find an optimal condition of polishing of tantalum stents and to obtain a better quality of the surface of tantalum stents. The as-received materials were non-polished tantalum stents. The polishing cell was designed similar to that for nitinol alloy material mentioned before. A glass container (100 ml) was used as an electrolyte container. A DC rectifier (Polipower Struers) was employed as a power supply. For cathode, a graphite stick was chosen with a diameter of 10 mm. Several electrolytes were selected for this study, as shown in Table 10.

TABLE 10

The selected electrolytes for polishing tantalum stents

| Solution (% concentration) | Volumes |
|---|---|
| (I) acetic acid (99.8%) | 20 ml |

TABLE 10-continued

The selected electrolytes for polishing tantalum stents

| Solution (% concentration) | Volumes |
|---|---|
| $H_2SO_4$ (95-97%) | 50 ml |
| HF (48-51%) | 10 ml |
| (II) $H_2SO_4$ (95-97%) | 90 ml |
| HF (48-51%) | 10 ml |
| (III) $H_2SO_4$ (95-97%) | 50 ml |
| $HNO_3$ (65%) | 20 ml |
| HF (48-51%) | 20 ml |

The electrolytes (I) and (II) were used for electrochemical polishing, and the electrolyte (III) was used for chemical polishing. The as-received samples were first cleaned with an alkaline solvent with detergent additive dipped in an ultrasonic bath for more than ten minutes. All the samples were then cleaned in distilled water with an ultrasonic agitation device for more than ten minutes. After degreasing, the samples were treated by means of acidic pickling for several periods of time: 2.5, 5, 7.5, 10 and 20 minutes in the following solution: HF 48-51% 5.6 ml, $H_2SO_4$ 95-97% 1 ml, $HNO_3$ 65% 8 ml, $H_2O$ 8 ml. The samples were then cleaned in distilled water with an ultrasonic agitation device for more than ten minutes. According to the effects observed by means of optical microscopy, ten minutes was chosen as the best pickling time. After pickling, the samples were polished with the selected electrolytes. The conditions are given in Table 11.

TABLE 11

The conditions for polishing tantalum stents

| Electrolyte | Applied voltage (V) | Time (min.) |
|---|---|---|
| Electrolyte (I) | 2.5, 5, 7.5, 10 | 2 |
| | 5 | 0.5, 1, 2, 3 |
| Electrolyte (II) | 15 | 3, 6, 9, 12 |
| | 10, 15, 20 | 9 |
| Electrolyte (III) | | 2, 4, 6 |

The voltage was selected as the controlling parameter because the current density was difficult to determine with the specific shape of the stents. The electropolishing of the as-received samples without degreasing and pickling was also done in order to check whether or not an oxide layer exists on the surface as well as to investigate the effects of pickling on the electrochemical polishing of the stents. The conditions are shown in Table 12.

TABLE 12

The conditions and the result of electropolishing tantalum stents without degreasing and pickling

| Electrolyte | Applied voltage (V) | Time (min.) | Result |
|---|---|---|---|
| Electrolyte (I) | 5 | 2 | Bad |
| Electrolyte (II) | 15 | 9 | Bad |

After cleaning in distilled water with an ultrasonic agitation device for more than ten minutes, all the polished samples were evaluated with optical microscopy and some of them were then studied by means of scanning electron microscopy. The SEM pictures of both the polished samples and the as-received samples were taken in order to compare their surface qualities.

Comparison Among the Different Polishing Methods

Table 13 summarizes all the results of the explored polishing processes for the tantalum stents. All these electrochemical polishing processes were conducted at room temperature with agitation. Prior to the electropolishing processes, both degreasing and pickling were done. Two electrolytes were explored for electropolishing: (I) acetic acid 20 ml, $H_2SO_4$ 50 ml, HF 10 ml, (II) $H_2SO_4$ 90 ml, HF 10 ml.

TABLE 13

The comparison of the different polishing processes

| Process | Electrolyte | Applied Voltage (V) | Time (min.) | Result |
|---|---|---|---|---|
| Electropolishing | Electrolyte (I) | 2.5 | 2 | general |
| | | 5 | | better |
| | | 7.5 | | good |
| | | 10 | | overpolished |

TABLE 13-continued

The comparison of the different polishing processes

| Process | Electrolyte | Applied Voltage (V) | Time (min.) | Result |
|---|---|---|---|---|
| | | 5 | 0.5 | less polished |
| | | | 1 | general |
| | | | 2 | good |
| | | | 3 | overpolished |
| | Electrolyte (II) | 15 | 3 | less polished |
| | | | 6 | general |
| | | | 9 | good |
| | | | 12 | overpolished |
| | | 10 | | less polished |
| | | 15 | 9 | good |
| | | 20 | | general |
| Chemical polishing | Electrolyte (III) | | 2 | rough |
| | | | 4 | rough |
| | | | 6 | rough |

From the evaluation of the effects of polishing by means of optical microscopy, electrolyte (I) gave a relatively better effect; therefore it was concluded to be the preferred electrolyte.

The voltages 2.5 V, 5 V, 7.5 V and 10 V were explored respectively with electrolyte (I) for 2 min. The voltages of 2.5 and 10 V provided relatively bad results. 5 V revealed the best results among these voltages. Fixing the voltage to 5 V, the times 0.5 min., 1 min. and 3 min. were selected in order to compare the results. The result was that the voltage 5 V and the time 2 min. in conjunction with electrolyte (I) were optimal parameters for electrochemical polishing this kind of tantalum stents. Electrolyte (II) was also used with some changed parameters. Several times were explored with fixed voltage 15 V. It was found that 9 min. causes the best result among these times, and either 3 min. or 12 min. resulted in a bad surface quality. Then the time 9 min. was fixed and voltages were changed to explore their effects on the polishing. 15 V gave a relatively better result than 10 V and 20 V. Similar to the results in the experiment of polishing nitinol alloy materials, chemical polishing could not lead to a sufficient smooth surface. The conditions and the results were summarized in Table 13.

Based on the performed tests, the electrolyte solution used for electrochemically polishing tantalum comprises at least sulfuric acid and hydrofluoric acid, and optionally at least one carboxylic acid, in particular acetic acid. In a preferred embodiment, the electrolyte solution comprises sulfuric acid and hydrofluoric acid in a concentration corresponding to the sulfuric acid and hydrofluoric acid concentrations in a mixture of 70 to 120 volume parts of a 95 to 97% by weight sulfuric acid solution and 5 to 20 volume parts of a 48 to 51% by weight hydrofluoric acid solution, and more particularly in a concentration corresponding to the sulfuric acid and hydrofluoric acid concentrations in a mixture of about 90 volume parts of a 95 to 97% by weight sulfuric acid solution and about 10 volume parts of a 48 to 51% by weight hydrofluoric acid solution. In a further preferred embodiment, the electrolyte solution comprises sulfuric acid, hydrofluoric acid and acetic acid in a concentration corresponding to the sulfuric acid, hydrofluoric acid and acetic acid concentrations in a mixture of 20 to 80 volume parts of a 95 to 97% by weight sulfuric acid solution, 5 to 20 volume parts of a 48 to 51% by weight hydrofluoric acid solution and 10 to 30 volume parts of a 99.8% by weight acetic acid solution, and more particularly in a concentration corresponding to the sulfuric acid, hydrofluoric acid and acetic acid concentrations in a mixture of about 50 volume parts of a 95 to 97% by weight sulfuric acid solution, about 10 volume parts of a 48 to 51% by weight hydrofluoric acid solution and about 20 volume parts of a 99.8% by weight acetic acid solution.

Influence of Sample Preparation with Degreasing and Pickling on Electrochemical Polishing The conditions and the results of electrochemical polishing with no pickling were summarized in Table 12. SEM evaluation of the stent surface electrochemically polished without degreasing and acidic pickling showed disappointing results. It was clear that the rough oxide layers still adhered to the side surface of the stent. The surface of the polished sample reveals a worse quality than that of the as-received one. Thus, it can be concluded that the heavy oxide layer can not be removed only by means of electrochemical polishing, i.e. the preparation of pickling is necessary before electrochemical polishing the tantalum stents which are covered with heavy rough oxide layers. Degreasing was accomplished by an alkaline solvent with detergent additive. Pickling was used to remove the heavy oxide layer and normally done with alkaline or acidic solutions. In this experiment, acidic pickling was explored at room temperature with acidic solutions: HF 48-51% 5.6 ml, $H_2SO_4$ 95-97% 1 ml, $HNO_3$ 65% 8 ml, $H_2O$ 8 ml.

Several time periods were selected. The description of the effects of this pickling process was summarized in Table 14.

TABLE 14

The effects of acidic pickling for preparation of electropolishing stents

| | Time (min.) | | | | |
|---|---|---|---|---|---|
| | 2.5 | 5 | 7.5 | 10 | 20 |
| Result | no change | no change | general | good | overpickled |

For the immersion times 2.5 min. and 5 min., there were no apparent changes on the surface compared to that of the as-received samples by observation with optical microscopy, whereas for a time more than 7.5 min. some precipitates began to appear in the solutions during the experiment. The immersion time 20 min. caused attack on the surface. Thus, the pickling time should be controlled seriously in order to remove all the oxide layers and to avoid surface attack. In this study 6 min. was found to have a relatively good effect.

Electrochemical Polishing: Conclusions Nitinol

For nitinol a pre-treatment using a solution of 2 ml of hydrofluoric acid and 40 ml of nitric acid (14 M) for 5 to 7 minutes is suggested. For electrochemical polishing optimal results were found with 5 ml of perchloric acid (70%) and 100 ml of acetic acid (99.8%) using an anodic current of 0.15 amp and a voltage of 20 V during 1 to 3 minutes (Table 7).

Tantalum

For tantalum a solution of 20 ml of acetic acid, 50 ml of hydrosulphate and 10 ml of hydrofluoride or a solution of 90 ml of hydrosulphate and 10 ml of hydrofluoride was used. The voltage was 5 V during a period of 1 to 5 minutes and the pre-treatment was done using a solution of 5.6 ml of hydrofluoride (48-51%), 1 ml of hydrosulphate (95-97%), 8 ml of hydronitrate and 8 ml of water during 5 to 7 minutes (Table 15).

TABLE 15

The optimal conditions for electropolishing the tantalum stents

| Electrolyte | Applied voltage (V) | Time (min.) |
|---|---|---|
| Electrolyte (I)*** | 5 | ~2 |

***acetic acid 20 ml, $H_2SO_4$ 50 ml, HF 10 ml

This treatment resulted in a further reduction of thrombogenicity, of foreign body reaction and of prosthesis narrowing. These inventions can be used for any stent or endovascular prosthesis made of nitinol or tantalum.

4) Turning a Metallic Endovascular Prosthesis More Biocompatible Using a Titaniumnitride Coating A metal prosthesis always causes a kind of foreign body reaction after intraluminal implantation.

To improve the biocompatibility of the prosthesis, fine coatings can be applied. In a preferred embodiment of the invention, the prostheses are covered with a titanium nitride coating showing a thickness of between 0.1 and 500 μm and preferably a thickness of between 1 and 10 μm. Experiments with titanium nitride coatings (1-15 μm) showed a significantly decreased foreign body reaction in a porcine coronary model, what did result in a significant amelioration of the minimal luminal diameter of the prosthesis at follow-up.

Description of the Titanium Nitride Coating. Evaluation of the Tin Coated Endovascular Prosthesis in a Porcine Coronary Model Titanium nitride (TiN) coatings have proved their efficiency in increasing the lifetime of cutting tools. Their tribological properties are widely known and their use in bioengineering applications as a biomaterial has been considered, particularly as a wear-resistant coating for Ti6A14V orthopedic implants. The tests undertaken showed that wear was reduced, that the TiN friction coefficient was low and that TiN presented good chemical stability.

The present inventors used TiN (5 μm) to coat an intraluminal prosthesis and demonstrated improved biocompatibility.

To illustrate the invention a coronary stent of a coil-type design, as described in U.S. Pat. No. 5,183,085 was used. It consisted of a preconditioned, non ferromagnetic, highly polished stainless steel wire (AISI 316L) with a diameter of 0.18 mm. This design allows folding (radial compression) on any conventional balloon, resulting in a low profile 6F guiding catheter compatible stent delivery system. Percentage of axial shortening upon expanding the balloon is less than 5% and the stent is available in lengths from 12 mm up to 40 mm allowing customized stenting. These stents are available as bare stents or as mounted stents. In the present example stents of a length of 16 min were used. For this invention any laser cut stainless steel mesh stents or any intraluminal metal prosthesis can be used as well.

Porous Tin Coating

The vacuum deposition techniques of physical vapor deposition (PVD) and chemical vapor deposition (CVD) are well known for their ability to form TiN coatings of different structures and stoichiometries. Porous TiN can be generated in a reactive sputtering process, which is a special PVD method.

In the reactive sputtering process, Ar ions are produced by a glow discharge and accelerated against a Ti target. The ions impinging on the Ti lead to the ejection of particles from the target surface. These particles condense on the surfaces in line-of-sight to the target. Additional $N_2$ gas activated in the plasma and the Ti react to yield TiN. The structure of the TiN can be influenced and determined by controlling the deposition parameters like Ar and $N_2$ pressure, target power, substrate bias voltage, and substrate position relative to the Ti target. For certain parameters, the TiN layer grows with columnar structure and shows up to 1000 fold increase in effective surface area. The thickness of the sputtered layer lies around 5 μm. The thickness constancy is ensured by a uniform rotation of the intraluminal prosthesis during the sputtering process.

Experimental Work

The TiN coated and bare non-coated stents were radially compressed on a balloon catheter (3 to 3.5 mm) and randomly implanted in a series of coronary arteries of 20 domestic cross bred pigs of both sexes, weighing 25 to 30 kg. Ten TiN coated stents and 10 non-coated highly polished stainless steel stents were implanted for comparison. All stent deployments and implantations were successful and resulted in properly stented vessel segments. Six weeks after implantation, control angiography of the stented vessels was performed and subsequently pigs were sacrificed. At that time their average weight was about 70 kg and the vessels had also grown considerably, compared to their size at the time of implantation.

Angiographic analysis (quantitative coronary angiography) of stented vessel segments was performed before stenting, immediately after stenting, and at follow-up using the Polytron 1000-system as described by De Scheerder et al. in the Journal of Invasive Cardiology 1996; 8:215-222. The lumen diameters of the vessels were measured before stent implantation (=pre-stenting artery diameter values), immediately thereafter (=post-stenting values) and at follow-up (=diameters after 6 weeks). The degree of oversizing (%) was expressed as measured maximum balloon size minus minimal stent lumen diameter (measured 15 minutes after stent implantation) and divided by measured maximum balloon size. The late loss value is an indication of hyperplasia and is the difference between the post-stenting value and the diameter at follow-up. The results of the angiographic measurements are summarized in Table 16. Baseline selected arteries, measured balloon diameter and post stenting diameter were similar for the three types. Oversizing and recoil were also similar. At six weeks follow-up a larger minimal luminal stent diameter and a decreased late loss was found for the TiN-coated stents.

TABLE 16

Quantitative Coronary Analysis of titanium nitride coated stents

| Mean Artery Diameter (mm) | Non-coated stent n = 10 | TiN-coated stent n = 10 |
| --- | --- | --- |
| Pre stenting (mm) | 2.52 ± 0.18 | 2.53 ± 0.27 |
| Balloon size (mm) | 2.93 ± 0.16 | 2.94 ± 0.15 |
| Post stenting (mm) | 2.68 ± 0.16 | 2.71 ± 0.18 |
| Oversizing (%) | 16 ± 6 | 16 ± 7 |
| Recoil (%) | 8 ± 4 | 8 ± 4 |
| 6 weeks FU (mm) | 2.52 ± 0.29 | 2.69 ± 0.24 |
| Late loss | 0.16 ± 0.28 | 0.02 ± 0.16 |

After the pigs were sacrificed, coronary segments were carefully dissected together with 10 mm minimum vessel segment both proximal and distal to the stent. Histopathology, as evaluated by light microscopic examination, was performed on very thin cross-section slices of the stented artery sections. Injury of the arterial wall, due to stent deployment, was evaluated as a first factor and graded according to the method of Schwartz et al. (J. Am. Coll. Cardiol 1992; 19:267-274). Likewise, inflammatory reaction at every stent filament site was examined (second factor) by searching for inflammatory cells and graded as well. Appearance of thrombus was evaluated as a third factor and graded. The mean value of every factor for the 10 samples of each of the two stent types was calculated.

Thrombus formation was decreased in the coated stent group. Also peri-stent inflammation was decreased in the TiN-coated stent group.

Finally, a morphometric study was carried out on the stented vessel segments at the time of follow-up after six weeks of implantation. The study was made using a computerized morphometry program (Leitz CBA 8000). Measurements of lumen area, lumen inside the internal elastic lamina (=IEL area) and lumen inside the external elastic lamina (=EEL area) were performed on the arterial sites, all in mm2. Neointimal hyperplasia (=IEL area minus lumen area) and area stenosis in % as the ratio of hyperplasia to IEL area were derived therefrom. The results are shown in Table 17.

TABLE 17

Morphometry of titanium nitride coated stents

| Mean Cross Section Area (mm$^2$) | Non-coated stent n = 10 | TiN-coated stent n = 10 |
| --- | --- | --- |
| Lumen area (mm$^2$) | 1.71 ± 0.66 | 2.86 ± 0.74 |
| IEL area (mm$^2$) | 3.87 ± 1.39 | 3.81 ± 1.02 |
| EEL area (mm$^2$) | 5.74 ± 2.06 | 5.86 ± 2.12 |
| Hyperplasia (mm$^2$) | 2.16 ± 1.48 | 0.95 ± 0.64 |
| Area stenosis (%) | 54 ± 15 | 25 ± 11 |

TiN-coated stents showed an improved lumen area and a decreased neointimal hyperplasia and area stenosis at follow-up. Although the invention has been described for coronary blood vessels, similar results can be obtained for stents and intraluminal prosthesis with a TiN-coating in other luminal life stream conducts in animal and human bodies.

5) A Local Intraluminal Medicine or Gene Releasing System

Several trials with systematically (oral or intravenous) administered anti restenotic medicines after dilatation of narrowed lumina (for example of a coronary arterial atherosclerotic narrowing) failed in consequence of a too limited medicine concentration on the place where the medicine has to act and due to the systemic medicine's side effects when higher doses are administered. For this reason medicines were applied locally, at the place of the organ to be treated. For example in the treatment of coronary stenoses using special catheters, medicines were injected into the vessel wall.

Disadvantages of this approach are the limited efficiency of the so called local treatment (less than 5% of the administered medicine reaches the target organ) and the increased damage to the target organ due to the local drug administration.

Another method is the covering of an endoluminal prosthesis with a polymer coating and the impregnation of the polymer with a medicine. The disadvantage of this method is the limited capacity of the coating and the too fast release of the medicine.

To optimize this system the present inventor have made holes in the endoluminal prosthesis which holes have either a bottom or extend through the prosthesis. These holes are filled with the medicine impregnated polymer before implantation. The holes can vary in size and density. The condition is that the radial force of the prosthesis is not affected. By applying this technique an increment of the local medicine capacity of the prosthesis with a factor of one hundred and a considerable prolongation of the duration of medicine release can be obtained (weeks instead of days). Animal experimental research showed a hundredfold tissue concentration of the medicine in a porcine model after implantation of a polymer coated perforated endoluminal prosthesis in coronary arteries.

Furthermore the duration of medicine release was significantly longer and the presence of the medicine in the vascular tissue was significantly longer.

Polymeric drug eluting surface coatings have been described to improve stent biocompatibility by locally releasing the drug at the target site (EP-A-0 623 354).

Disadvantages of this system are:
1) the moderate biocompatibility of the polymers used, resulting in an increased inflammatory reaction,
2) because only very thin polymer layers can be used and the contact area is large, the drug release using these coated stents is too fast and because only very thin polymer layers can be applied the total dose of drug loaded on the stent to be locally released is limited.

By making holes in the metal structure of the prosthesis, which holes show either a bottom or extend right through the metal structure of the prosthesis, (FIG. 2) and filling these holes with a drug or a polymer coating containing one or more medicines with anti thrombotic and/or anti restenotic properties, a prosthesis is developed that very efficiently releases the medicine gradually and puts the medicine directly in contact with the damaged tissue. The prosthesis starts to function as a reservoir for the medicine, which is gradually released after implantation of the endoluminal prosthesis to carry out its function.

Instead of conventional medicines also genes can be used that code for certain substances (proteins) having either an anti thrombotic or an anti restenotic action.

Three significant advantages are obtained by using the prosthesis provided with holes in comparison with the classical polymer covered prostheses:
1) The total dose of medicine that can be loaded onto the prosthesis increases with a factor of one hundred to one thousand, depending on the size and the amount of holes.
2) By making holes showing a bottom, i.e. non-perforating holes, the medicine release can be directed; either towards the tissue surrounding the lumen or towards the lumen itself.
3) The release time of the medicine becomes much longer (weeks instead of days).

After having made the prosthesis, the therapeutic agent, i.e. a medicine or genes is to be applied onto the prosthesis, in particular into the holes provided on its surface. This can be done by dipping and/or spraying, after which the therapeutic agent applied next to the holes can optionally be removed. The therapeutic agent can either be applied as such or as a solution. In a preferred embodiment, it is however combined with a polymer which increases the adherence to the prosthesis and which can be used to control the release properties of the therapeutic agent. In a preferred embodiment there is applied to the body of a prosthesis and in particular to its tissue-contacting outer surface, a solution which includes a solvent, a polymer dissolved in the solvent and a therapeutic substance (i.e. a drug) dispersed in the solvent, and the solvent thereafter is evaporated to leave a drug eluting polymeric substance filling the holes of the prosthesis. The inclusion of a polymer in intimate contact with a drug filling up the holes of the prosthesis allows the drug to be retained in the prosthesis in a resilient matrix during expansion of the prosthesis and also slows the administration of drug following implantation. This method can be used whether the perforated prosthesis has a metallic or polymeric surface. The method is also an extremely simple one since it can be effected by simply immersing the perforated prosthesis into the solution or by spraying the solution onto the perforated prosthesis. The amount of drug to be included in the perforated prosthesis can be readily controlled by changing the size and the amounts of the holes and/or perforations or by using different drug concentrations and or different coating application methods. The rate at which the drug is delivered can be controlled by the selection of an appropriate bioabsorbable or biostable polymer and by the ratio of drug to polymer in the solution. By this method, drugs such as glucocorticoids (e.g. methylprednisolone, dexamethasone, betamethasone), heparin, hirudin, tocopherol, angiopeptin, aspirin, ACE inhibitors, Cytochalasin A, B, and D, Trapidil, Paclitaxel, Rapamycin, Actinomycin, growth factors, oligonucleotides, and, more generally, antiplatelet agents, anticoagulant-agents, antimitotic agents, antioxidants, antimetabolite agents, and anti-inflammatory agents and also genes can be stored in a perforated prosthesis, retained in a perforated prosthesis during expansion of the perforated prosthesis and elute the drug at a controlled rate. The release rate can be further controlled by using additional barrier coatings or multiple layers of coating with varying drug concentrations. In operation, the perforated prosthesis made according to the present invention can deliver drugs to a body lumen by introducing the perforated prosthesis transluminally into a selected portion of the body lumen and radially expanding the perforated prosthesis into contact with the body lumen. The transluminal delivery can be accomplished by a catheter designed for the delivery of perforated prostheses and the radial expansion can be accomplished by balloon expansion of the perforated prosthesis, by self-expansion of the perforated prosthesis or a combination of self-expansion and balloon expansion.

The underlying structure of the perforated prosthesis used according to the invention can be virtually any perforated prosthesis design, for example of the self-expanding type or of the balloon expandable type, and of metal or polymeric material. Thus metal prosthesis designs such as those disclosed in U.S. Pat. No. 4,733,665 (Palmaz) and U.S. Pat. No. 5,603,721 (Lau) could be used in the present invention. The perforated prosthesis could be made of virtually any biocompatible material having physical properties suitable for the design. For example, tantalum, nitinol and stainless steel have been proven suitable for many such designs and could be used in the present invention. Also, prostheses made of biostable or bioabsorbable polymers such as poly(ethylene terephthalate), polyacetal, poly(lactic acid), poly(ethylene oxide)/poly(butylene terephthalate) copolymer could be used in the present invention. Although the perforated prosthesis surface should be clean and free from contaminants that may be introduced during manufacturing, the perforated prosthesis surface requires no particular surface treatment in order to retain the coating applied in the present invention.

To coat the perforated prosthesis, in particular to fill the holes made therein, the following method can be followed. A solution which includes a solvent, a polymer dissolved in the solvent and a therapeutic substance dispersed in the solvent is first prepared. The solvent, polymer and therapeutic substance should be mutually compatible. The solvent should be capable of placing the polymer into solution at the concentration desired. Moreover the solvent and polymer should not chemically alter the therapeutic character of the therapeutic substance. However, the therapeutic substance only needs to be dispersed throughout the solvent so that it may be either in a true solution with the solvent or dispersed in fine particles in the solvent. Examples of some suitable combinations of polymer, solvent and therapeutic substance are set forth in Table 18.

TABLE 18

Examples of some suitable combinations of polymers, solvents and therapeutic substances

| Polymer | Solvent | Therapeutic substance |
|---|---|---|
| poly(L-lactic acid) | chloroform | dexamethasone |
| poly(lactic acid-co-glycolic acid) | acetone | dexamethasone |
| polyether urethane | N-methyl pyrrolidone | tocopherol (vitamin E) |
| silicone adhesive | xylene | dexamethasone phosphate |
| poly(hydroxybutyrate-co-hydroxy-valerate) | Dichloromethane | Asprin |
| fibrin | Water (buffered saline) | heparin |

The solution is applied to the perforated prosthesis and the solvent is allowed to evaporate, thereby filling the perforations and leaving on the perforated prosthesis surface a coating of the polymer and the therapeutic substance. Typically, the solution can be applied to the perforated prosthesis by either spraying the solution onto the perforated prosthesis or immersing the perforated prosthesis in the solution. Whether one chooses application by immersion or application by spraying depends principally on the viscosity and surface tension of the solution. After having coated the prosthesis, the prosthesis can optionally be cleaned to remove the coating applied next to the holes leaving only the therapeutic agent present in the holes onto the prosthesis.

The polymer chosen should be a polymer that is biocompatible and minimizes irritation to the vessel wall when the perforated prosthesis is implanted. The polymer may be either a biostable or a bioabsorbable polymer depending on the desired rate of release or the desired degree of polymer stability, but a bioabsorbable polymer may be more desirable since, unlike a biostable polymer, it will not be present long after implantation to cause any adverse, chronic local response. Bioabsorbable polymers that could be used include poly(L-lactic acid), polycaprolactone, poly(lactide-co-glycolide), poly(hydroxybutyrate), poly(hydroxyburytate-co-valerate), polydioxanone, polyorthoester, polyanhydride, poly(glycolic acid), poly(D, L-lactic acid), poly(glycolic acid-co-trimethylene carbonate), polyphosphoester, polyphosoester urethane, poly(amino acids), cyanoacrylates, poly (trimethylene carbonate), poly(iminocarbonate), copoly (etheresters) (e.g. PEO/PLA) polyalkylene oxalates, poly (organs)phosphazenes, hydrophylic polymetracrylates and biomolecules such as fibrin, fibrinogen, cellulose, starch, collagen and hyaluronic acid. Also, biostable polymers with a relative low chronic tissue response such as polyurethanes, silicones, and polyesters could be used and other polymers could also be used if they can be dissolved and cured or polymerized on the perforated prosthesis such as polyolefins, polyisobutylene and ethylene-alphaolefin copolymers; acrylic polymers and copolymers, vinyl halide polymers and copolymers, such as polyvinyl chloride; polyvinyl ethers, such as polyvinyl methyl ether; polyvinylidene halides, such as polyvinylidene fluoride and polyvinylidende chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, actrylonitrile-styrene copolymers, ABS resins, and ethylene-vinyl acetate copolymers; polyamides, such as Nylon 66 and polycaprolactam; alkyl resins; polycarbonates: polyoxymthylenes; polyimides; polyethers; epoxy resins, polyurethanes; rayon; rayon-triacetate; cellulose, cellulose acetate, cellulose butyrate; cellulose acetate butyrate; cellophane; cellulose nitrate; cellulose propionate; cellulose ethers, carboxymethyl cellulose and hydrophylic polymetacrylates. The ratio of therapeutic substance to polymer in the solution will depend on the efficacy of the polymer in securing the therapeutic substance into the perforated prosthesis and the rate at which the coating is to release the therapeutic substance to the tissue of the blood vessel or body conduit. More polymer may be needed if it has relatively poor efficacy in retaining the therapeutic substance in the perforated prosthesis and more polymer may be needed in order to provide an elution matrix that limits the elution of a very soluble therapeutic substance. A wide ratio of therapeutic substance to polymer could therefore be appropriate and the weight ratio could range from about 10:1 to 1:100. The therapeutic substance could be virtually any therapeutic substance which possesses desirable therapeutic characteristics for application to a blood vessel or body conduit. This can include both solid substances and liquid substances. For example, glucocorticoids (e.g. methyl prednisolone, dexamethasone, betamethasone), heparin, hirudin, tocopherol, angiopeptin, aspirin, Cytochalasin A, B, and D, Trapidil, Paclitaxel, Rapamycin, Actinomycin, ACE inhibitors, A2 blockers, beta blockers, growth factors, oligonucleotides, and, more generally, antiplatelet agents, anticoagulant agents, antimitotic agents, antioxidants, antimetabolite agents, and anti-inflammatory agents could be used. Antiplatelet agents can include drugs such as aspirin and dipyridamole. Anticoagulant agents can include drugs such as heparin, coumadin, protamine, hirudin and tick anticoagulant protein. Antimitotic agents and antimetabolite agents can include drugs such as methotrexate, azathioprine, vincristine, vinblastine, fluorouracil, adriamycin and mitomycin. Furthermore this perforated prosthesis can be used to deliver genes that code for substances that can influence the foreign body reaction to the prosthesis or modify the healing response induced by tissue damage.

Figure 14:
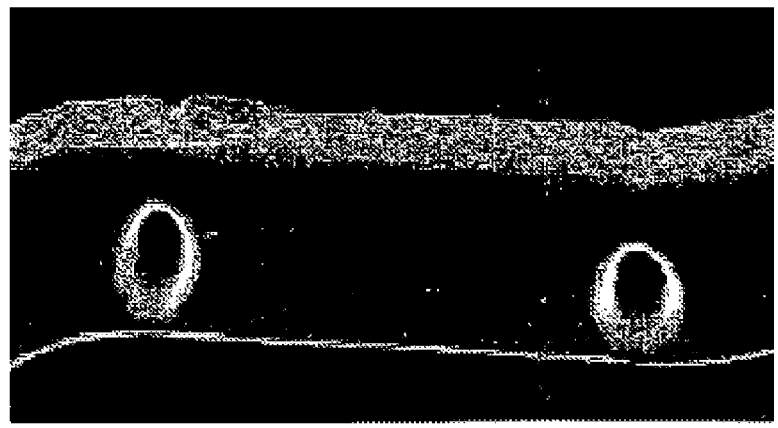
FIG. 14 is a scanning electron microscope picture (156×) showing a perforating hole of the same type as illustrated in FIG. 9.

Description of the Perforated Prosthesis in Order to Obtain an Improved Local Drug Delivery Device To illustrate the invention a tubular laser cut balloon expandable stent was used (FIGS. 1 and 2). Perforating holes of 50 μm were made, i.e. holes extending entirely through the stent, using the same water-guided eximer laser as described in the first part of this description at a frequency of 100 Hz, pulse duration of 0.15 ms and a voltage of 510 volts. In this way the holes can easily be made in the same operation as the cutting of the prosthesis out of the tubular member. Other methods can however also be used to make the holes, for example mechanical die cutting or conventional laser cutting techniques. FIG. 14 shows a microscopic picture of a part of the obtained prosthesis. After conventional electrochemical polishing the stents were dipped in a polymer solution in which the drug was dissolved. In this example use was made of a fluorinated polymethacrylate (PFM-P75) in which 10% methyl prednisolone was dissolved. Total loading dose of methyl prednisolone loaded on a PFM-P75-coated non perforated stents was 10 μg. Total loading dose of a perforated stent was 3500 μg.

In vitro release curves of the methyl prednisolone loaded PFM-P75-coated stents showed a gradually release of the methyl prednisolone over 3 weeks compared to 48 hours for the non perforated stents. Implantation of the methyl prednisolone loaded perforated stents in porcine coronary arteries using the same study protocol as for the TiN-coated stents demonstrated perfect biocompatibility of these stents. No inflammation surrounding the stent filaments was found at day 3, day 7 and day 14. At six weeks only a minimal neointimal hyperplasia was found. This invention can be used with all kinds of drug or gene containing polymers and also for direct coating of drugs or genes onto the prosthesis without the use of a polymer.

In general, the holes provided in the prosthesis do not have to extend through the prosthesis as in the previous example but show preferably a bottom in order to obtain a directional release of the therapeutic agent. Different types of holes are illustrated in the schematic drawings of FIGS. 9 to 13 and in the microscopic pictures of FIGS. 14 to 16. As already explained hereabove, the prosthesis comprises a tubular wall which is usually produced from solid sheet metal but which may also be made of a synthetic sheet material. The wall comprises cuts, usually around cut away portions, forming the struts 1 of which the prosthesis is composed. These struts have an outer or convex surface 2, arranged to engage after implantation the inner wall of the lumen, and an opposite inner or concave surface 3. In order to increase the therapeutic agent loading capacity of the prosthesis, holes 4 are made in the outer surface of the tubular wall. FIGS. 9 to 13 are cross-sectional views through a strut at the location of such a hole 4. As indicated on these figures, the strut has a strut width W and a thickness T, the longitudinal direction of the strut is indicated by reference A in FIG. 2.

At the outer surface of the strut, the holes 4 show an outer opening 5 which is situated at a distance from both longitudinal edges 10 of the strut. This outer opening has a width w measured perpendicular to the longitudinal direction A of the strut and a length l measured in this longitudinal direction. Since the edge of the opening 5 is somewhat beveled, the width and the length of the opening 5 is to be determined by drawing a line 11 along the inner wall of the hole 4 and determining the point of intersection with the outer surface plane so that the bevel of the upper edge of the hole 4 is not taken into account for determining the width and length of its outer opening 5. The same goes for the inner opening which will be described hereinafter in case of a perforating hole.

According to this aspect of the invention, the length l of the outer opening 5 should comprise at the most five times, and preferably at the most three times, the width w thereof whilst the hole 4 itself should extend over a depth d in the strut which is larger than 30%, preferably larger than 50%, and most preferably larger than 60%, of the thickness T of the strut 1. In this way, the therapeutic agent is distributed over a number of relatively small holes enabling a homogeneous distribution thereof over the surface of the prosthesis. The total amount of therapeutic agent applied onto the prosthesis can be controlled not only by the number of holes but also by the depth thereof. An advantage of providing deeper holes is that the surface of the outer opening 5 through which the therapeutic agent can be released is relatively small compared to the volume of the hole so that the duration of the therapeutic agent release can be extended.

The outer openings 5 have advantageously a width w larger than 10 μm, in particular larger than 20 μm and more particularly larger than 30 μm but smaller than 100 μm, preferably smaller than 60 μm and most preferably smaller or equal to 50 μm. The length of the outer openings 5 may comprise up to five times this width but is preferably substantially equal to the width w. The opening 5 is in particular preferably substantially circular.

In a preferred embodiment, the width w of the outer opening 5 comprises at the most 60%, preferably at the most 50%, of the width W of the strut 1. Together with the limited length l of the outer openings 5 this relatively small width enables to increase the depth d of the holes whilst maintaining the required minimum radial strength of the prosthesis.

As illustrated in FIG. 2, the openings are divided according to the longitudinal directions of the struts, i.e. they are not preferably not arranged next to one another in the transverse direction in order to have a minimal effect on the radial strength of the prosthesis. Preferably, the holes are arranged on substantially constant mutual distances to achieve a uniform distribution of the therapeutic agent.

Figure 9:
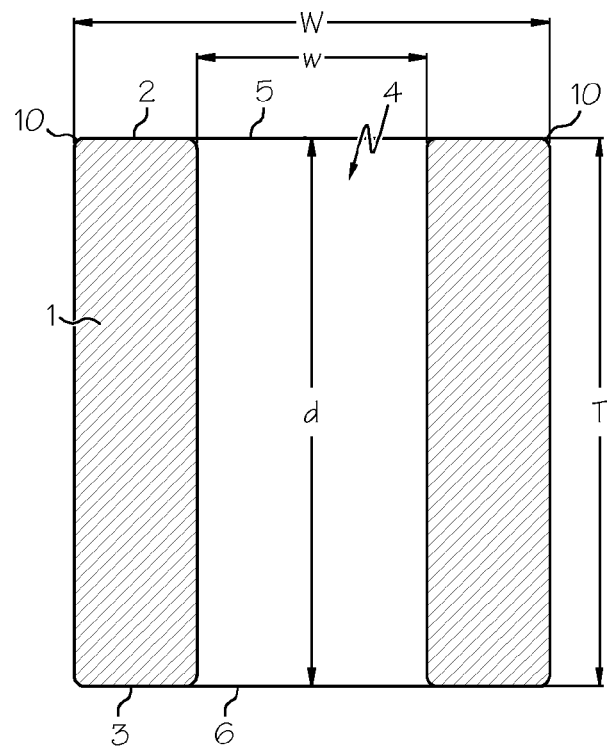
FIG. 9 shows, on a larger scale, a schematic cross-sectional view along lines VI-VI in FIG. 2, illustrating a perforating hole with a substantially cylindrical shape.

FIGS. 9 and 14 illustrate a perforating hole 4 forming at the inner surface 3 of the tubular prosthesis wall an inner opening 6 which is substantially as large as the opposite outer opening 5. Apart from the beveled edges, the hole 4 is substantially cylindrical. Such a hole 4 can easily be made by means of a laser beam, preferably by means of a liquid-guided laser beam by applying a total amount of cutting energy sufficient to produce such a hole without having to move the laser beam.

Figure 10:
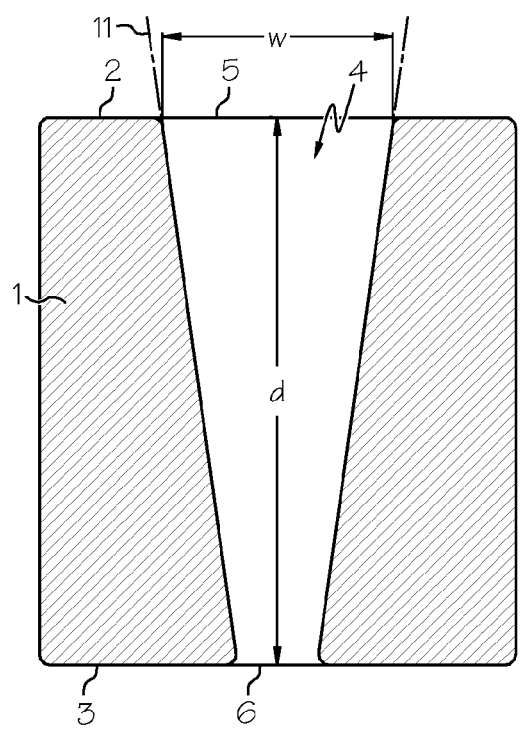
FIG. 10 is a view similar to FIG. 7 but showing a perforating substantially conical hole having a substantially circular outer opening and a smaller inner opening.

Referring now to FIGS. 9 and 10, the inner opening 6 has a first size and the outer opening 5 has a second size. As seen in both FIGS. 9 and 10, the width w of the hole 4 is no greater than at least one of the first size or the second size. The first size of the inner opening and the second size of the outer opening define the maximum width w of the hole 4 over its depth d.

Figure 12:
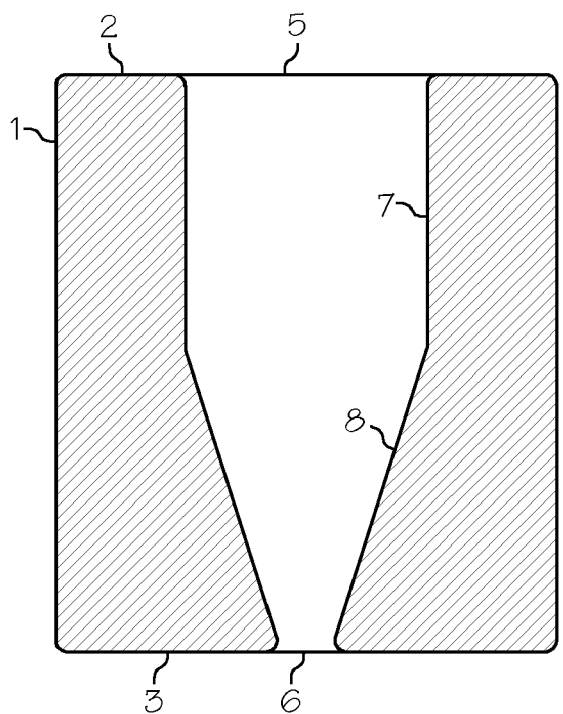
FIGS. 12 and 13 are views similar to the views of FIGS. 10 and 11 but showing another shape of holes.
Figure 15:
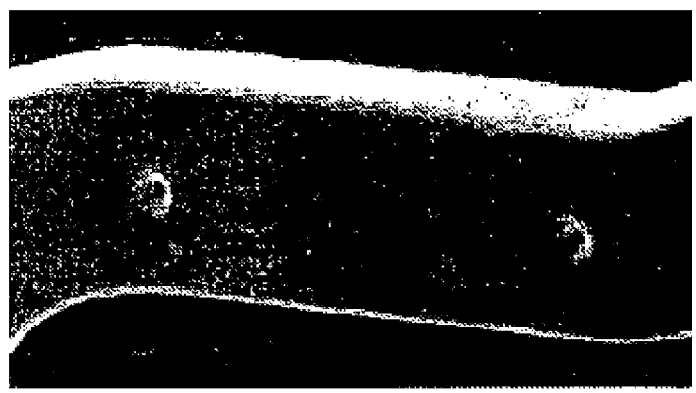
FIG. 15 is a scanning electron microscope picture (156×) showing a perforating hole of the same type as illustrated in FIG. 10.

FIGS. 10, 12 and 15 illustrate a perforating hole 4 which also form an inner opening 6 but which has the advantage that there is a more directional release of the therapeutic agent, i.e. more therapeutic agent is released towards the wall of the lumen than towards the interior thereof. This is due to the fact that the inner opening 6 is smaller than the outer opening 5. In FIG. 10, the hole narrows conically from the outer opening 5 towards the inner opening 6 and is thus substantially conical. In FIG. 12, the hole shows on the contrary first a substantially cylindrical portion 7 and subsequently a bottom portion 8 narrowing conically towards the inner opening 6. These two types of holes can also easily be made by means of a laser beam, preferably by means of a liquid-guided laser beam, without having to move the laser beam during the cutting operation. The different types of holes can in particular be controlled by adjusting the pulse width of the pulse laser beam, a greater pulse width producing a more elongated cone shape as in FIG. 10 whilst a smaller pulse width produces a shorter or steeper cone shape as in FIG. 12.

Figure 11:
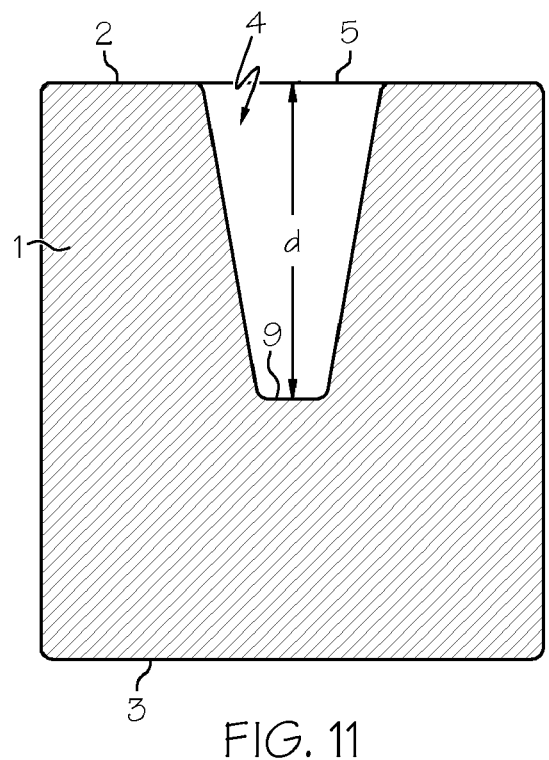
FIG. 11 is a view similar to FIG. 8 but the non-perforating conical hole does not extend through the strut but shows a bottom.
Figure 13:
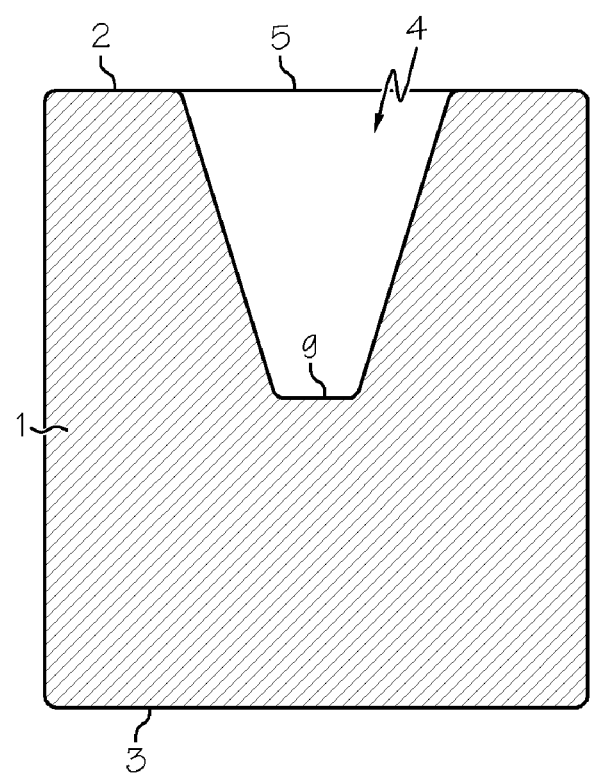
Figure 16:
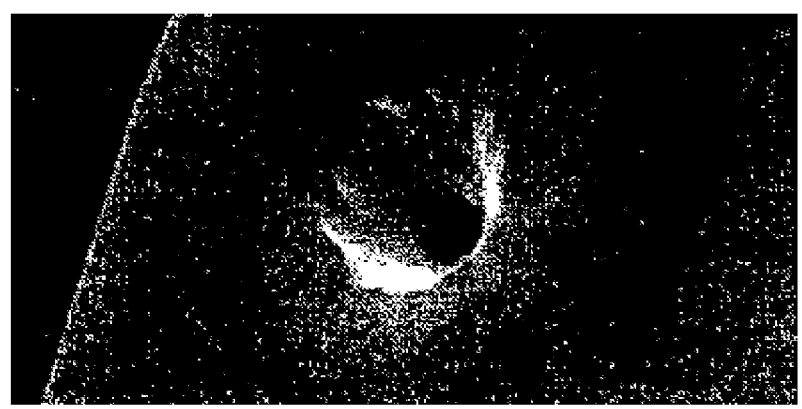
FIG. 16 is a scanning electron microscope picture (625×) showing a non-perforating hole, provided with a bottom, of the same type as illustrated in FIG. 11.

In the most advantageous embodiment, the total amount of energy of the laser beam is reduced so that the hole does not extend entirely through the strut but forms a bottom 9. Such a hole is illustrated in FIGS. 11, 13 and 16. In the illustrated embodiments, the hole is entirely conical or frusto-conical. It will however be clear that the hole could also show a conical bottom part and on top of that a more cylindrical part, depending on the thickness of the strut and the depth of the hole. From the shapes of the conical portions in the figures it will be clear that the hole illustrated in FIG. 11 can be achieved by means of a same type of laser beam as the hole illustrated in FIG. 10 whilst the hole illustrated in FIG. 13 can be achieved by means of the same type of laser beam as the hole illustrated in FIG. 12, the total amount of cutting energy, i.e. the duration of the cutting process being of course reduced to achieve a shallower hole.

The holes illustrated in the figures have all a substantially circular cross-section seen parallel to the outer or inner surface of the prosthesis. For making elongated holes, i.e. holes having a length l larger than their width w, two or more of the above described holes can be made next to one another to achieve one elongated hole.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

What is claimed is:

1. A radially expandable prosthesis comprising:
a tubular wall comprising a plurality of adjacent filaments, each filament having a plurality of adjacent segments, two adjacent segments defining a segment pair, segments of segment pairs having connected ends and unconnected ends, the connected ends connected to one another via a curved section, the curved section comprising a proximal turn or a distal turn, each segment having an inflection point along its length, wherein the segments of the segment pairs are separated from one another, in a circumferential direction, by a greater distance at their connected ends than at their unconnected ends;
a plurality of axial elements joining the adjacent filaments, each axial element consisting of a single continuous curve;
a plurality of reservoirs disposed within the adjacent filaments; and
a titanium nitride coating disposed on the tubular wall, wherein the titanium nitride coating has a thickness between 1 to 10 μm.

2. The prosthesis of claim 1, wherein the titanium nitride coating is porous.

3. The prosthesis of claim 1, wherein the reservoirs are holes extending through the entire thickness of the adjacent filaments.

4. The prosthesis of claim 1, wherein a plurality of reservoirs are disposed only within the adjacent filaments and there are no reservoirs in the connectors.

5. The prosthesis of claim 1, wherein each filament has an outer surface, an inner surface, and a thickness therebetween, and each reservoir comprises an opening in an outer surface of the strut that extends through only a portion of the thickness of the filament.

6. A radially expandable prosthesis comprising:
a tubular wall having an outer surface, an inner surface, and a thickness therebetween, the tubular wall comprising a plurality of interconnected serpentine bands including first bands and second bands, each band comprising adjacent segments, two adjacent segments defining a segment pair, segments of segment pairs having connected ends and unconnected ends, the connected ends connected to one another via a curved section, the curved section comprising a proximal turn or a distal turn, each segment having an inflection point along its length, wherein the segments of the segment pairs are separated from one another, in a circumferential direction, by a greater distance at their connected ends than at their unconnected ends;
the bands connected one to another via a plurality of connectors, each connector consisting of a single continuous curve having a first end and a second end, wherein the first end is circumferentially aligned with the second end along a common longitude;
the first bands being immediately adjacent to two second bands, the second bands being immediately adjacent to two first bands, each first band being out of phase with each second band;
the connectors extending between distal valleys and proximal peaks of immediately adjacent bands;
every third distal valley of each of the first and second serpentine bands having one of the connectors attached thereto;
the serpentine bands comprising a plurality of reservoirs; wherein the prosthesis has an electrochemically polished surface.

7. The prosthesis of claim 6, wherein the reservoirs are holes extending from the outer surface of the tubular wall, the reservoirs having a depth of at least 30% of the thickness of the tubular wall.

8. The prosthesis of claim 7, wherein the reservoirs have a depth of 50% of the thickness of the tubular wall.

9. The prosthesis of claim 7, wherein the reservoirs have a depth of 60% of the thickness of the tubular wall.

10. The prosthesis of claim 7, wherein the reservoirs extend through the entire thickness of the tubular wall.

11. The prosthesis of claim 6, wherein the reservoirs are filled with a therapeutic agent.

12. The prosthesis of claim 11, wherein at least one of the outer surface and the inner surface of the tubular wall is coated with a therapeutic agent.

13. The prosthesis of claim 6 further comprising a titanium nitride coating, wherein the titanium nitride coating has a thickness between 0.1 to 500 μm.

14. The prosthesis of claim 6, wherein the single continuous curve of each of the connectors has a connector peak.

15. The prosthesis of claim 14, wherein each of the connector peaks has the same orientation.

16. The prosthesis of claim 6, wherein a plurality of reservoirs are disposed only within the serpentine bands and there are no reservoirs in the connectors.

17. The prosthesis of claim 6, wherein the connectors connect one distal valley of the first band to a confronting proximal valley of the second band.

* * * * *